United States Patent
Caruana et al.

(10) Patent No.: US 10,364,212 B2
(45) Date of Patent: Jul. 30, 2019

(54) PROCESS FOR THE PREPARATION OF ENCLOMIPHENE CITRATE HAVING NEEDLE SHAPED CRYSTAL HABIT

(71) Applicant: F.I.S.—FABBRICA ITALIANA SINTETICI S.P.A., Montecchio Maggiore (VI) (IT)

(72) Inventors: Lorenzo Caruana, Montecchio Maggiore (IT); Pierluigi Padovan, Montecchio Maggiore (IT); Claudio Dal Santo, Sarego (IT)

(73) Assignee: F.I.S.—FABBRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 0 days.

(21) Appl. No.: 16/060,978

(22) PCT Filed: Apr. 22, 2016

(86) PCT No.: PCT/EP2016/059072
§ 371 (c)(1),
(2) Date: Jun. 11, 2018

(87) PCT Pub. No.: WO2017/182097
PCT Pub. Date: Oct. 26, 2017

(65) Prior Publication Data
US 2018/0362444 A1 Dec. 20, 2018

(51) Int. Cl.
| | | |
|---|---|---|
| C07C 217/16 | (2006.01) |
| C07C 51/41 | (2006.01) |
| C07C 59/265 | (2006.01) |
| A61P 3/10 | (2006.01) |
| A61P 15/08 | (2006.01) |
| C07C 217/18 | (2006.01) |

(52) U.S. Cl.
CPC ............. *C07C 217/18* (2013.01); *A61P 3/10* (2018.01); *A61P 15/08* (2018.01); *C07C 51/412* (2013.01); *C07B 2200/13* (2013.01); *C07C 59/265* (2013.01)

(58) Field of Classification Search
CPC ..... C07C 217/18; C07C 51/41; C07C 59/265; A61P 3/10; A61P 15/08
See application file for complete search history.

(56) References Cited

U.S. PATENT DOCUMENTS

| | | | |
|---|---|---|---|
| 2,914,563 A | 11/1959 | Allen et al. |
| 3,848,030 A | 11/1974 | Viterbo et al. |
| 5,118,832 A | 6/1992 | Pearson |
| 6,632,841 B1 | 10/2003 | Usin et al. |
| 7,368,480 B2 | 5/2008 | Podolski |
| 9,428,442 B2 | 8/2016 | Serafini |
| 2014/0163114 A1 | 6/2014 | Podolski |
| 2017/0349533 A1* | 12/2017 | Padovan ............... C07C 217/18 |

FOREIGN PATENT DOCUMENTS

| | | |
|---|---|---|
| CN | 103351304 A | 10/2013 |
| DE | 1155436 B | 10/1963 |
| DE | 2224240 A1 | 12/1972 |
| GB | 879792 A | 10/1961 |
| WO | 2014031177 A1 | 2/2014 |
| WO | 2015138340 A1 | 9/2015 |

OTHER PUBLICATIONS

International Search Report and Written Opinion for International Application No. PCT/EP2016/059072 (12 Pages) (dated Oct. 20, 2016).
Szumigala, Ronald H., et al., "Facile Synthesis of 2-Bromo-3-Fluorobenzonitrile: An Application . . .", The Journal of Organic Chemistry, vol. 69, No. 2, pp. 566-569, 2004.
Search Report issued in corresponding European Patent Application No. EP14190736, filed Oct. 14, 2015.
International Search Report issued in PCT Application No. PCT/EP2015/074746. (dated Apr. 6,2016) (6 pages).
E.M. Dolginova et al., "Synthesis and Biological Study of the cis- and trans-isomers of Clomiphene Citrate and Some Intermediates of its Synthesis", Pharmaceutical Chemistry Journal, 1984, vol. 18, No. 11, pp. 758-764.
F P Palopoli et al., "Substituted Aminoalkoxytriarylhaloethylenes", Journal of Medicinal Chemistry, 1967, vol. 10, pp. 84-86.
P. Narasimha Rao et al., "Synthesis of carbon-14 labeled clomiphene", Journal of Labelled Compounds and Radiopharmaceuticals, 1985, vol. 22, No. 3, pp. 245-255.
M J McLeish., "Clomiphene Citrate", Analytical Profiles of Drug Substances and Excipients, 1998, vol. 25, pp. 85-120.
A. Richardson et al., "Stereochemistries of geometric isomers of 4-(2-bromo-1, 2-diphenylvinyl) phenol, 4-(2-bromo-1, 2-diphenylvinyl) anisole, and 2-[p-(2-brorno-1,2-diphenylvinyl) phenoxy] triethylamine: Corrections of the literature", Journal of Pharmaceutical Sciences, 1976, vol. 65, No. 10, pp. 1545-1547.
S. Ernst et al., "(E)-1-[p-(Diethylaminoethoxy) phenyl]-1,2-diphenyl-2-chloroethylene Hydrochloride (Clomiphene Hydrochloride)", Acta Cryst, 1976, pp, 291-293.
D. Buno et al., "On Some Physiological and Pharmacological Effects of Clomiphene", Rev. Argent. Endocrinol. Metab., 1972, vol. 18, pp. 15-23.
Sigma-Aldrich Product Catalog "Enclomiphene hydrochloride", Retrieved from <https://www.sigmaaldrich.com/catalog/product/sigma/sm10719?lang=en&region=US>, 2018, 4 pages.
Chemical Abstract Service Registry Database Registry No. 39729-47-0 [Entered STN: Nov. 16, 1984].

* cited by examiner

*Primary Examiner* — Sun Jae Yoo

(74) *Attorney, Agent, or Firm* — Lucas & Mercanti, LLP

(57) ABSTRACT

An improved and well reproducible process for the preparation of Enclomiphene citrate having needle shaped crystal habit is provided. It is also related to a solid form of Enclomiphene citrate.

17 Claims, 9 Drawing Sheets

PROCESS FOR THE PREPARATION OF ENCLOMIPHENE CITRATE HAVING NEEDLE SHAPED CRYSTAL HABIT

CROSS-REFERENCE TO RELATED APPLICATIONS

This application is a 371 of PCT/EP2016/059072, filed Apr. 22, 2016.

TECHNICAL FIELD

The present invention relates to an improved process for the preparation of Enclomiphene citrate. Moreover, it is also related to a solid form of Enclomiphene citrate.

BACKGROUND ART

Enclomiphene citrate is an active pharmaceutical ingredient currently under evaluation in clinical phase III for the treatment of secondary hypergonadism. Moreover, it also could be potentially used for an adjuvant therapy in hypogonadal men with Type 2 diabetes.

Enclomiphene citrate of formula (I):

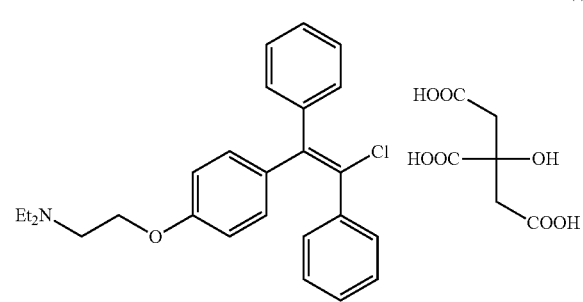

has chemical name of Ethanamine, 2-[4-[(1E)-2-chloro-1,2-diphenyl ethenyl]phenoxy]-N,N-diethyl-, 2-hydroxy-1,2,3-propanetricarboxylate (1:1); has CAS RN. 7599-79-3, and it is also named trans-Clomiphene monocitrate, E-Clomiphene citrate or Enclomiphene monocitrate.

Enclomiphene is component of Clomiphene, an active pharmaceutical ingredient, having chemical name Ethanamine, 2-[4-(2-chloro-1,2-diphenylethenyl)phenoxy]-N,N-diethyl, since Clomiphene is a mixture of the geometric isomers trans-Clomiphene (i.e. Enclomiphene) and cis-Clomiphene.

The U.S. Pat. No. 3,848,030, in examples 31 and 32, discloses a process for the resolution of the geometric isomers of Clomiphene through the preparation of salts with racemic binaphthyl-phosphoric acid.

In the later publication Acta Cryst. (1976), B32, pag. 291-293, the actual geometric isomery has been definitely established by single crystal X-Ray diffraction.

Finally, in the publication "Analytical profiles of drug substances and excipients", vol. 25, (1998), pag. 85-121, in particular at pag. 99, it is stated that prior to 1976 the cis stereochemistry was wrongly assigned to the trans-isomer of Clomiphene (E-Chlomiphene or Enclomiphene), and only after the above publication on Acta Cryst. the correct geometric isomery has been definitively assigned.

These observations in the prior art have been confirmed by our experimentation. In particular, repeating the experiment 31 of U.S. Pat. No. 3,848,030, the trans-Clomiphene salt with racemic binaphthyl-phosphoric acid was isolated and not the salt with cis-Clomiphene as stated in said patent, as confirmed by 2D H-NMR analysis (NOESY experiment).

Thus, Example 31 of U.S. Pat. No. 3,848,030, provides, at the end, Enclomiphene citrate, crystallized from a mixture of ethyl ether and ethanol, having a m.p. of 133-135° C. Example 32, instead provided Cis-Clomiphene citrate, crystallized from a mixture of ethyl ether and ethanol, having a m.p. of 120-126° C.

Thus, with the aim of preparing Enclomiphene citrate, whole experiment 31 of U.S. Pat. No. 3,848,030 has been reworked also carrying out the crystallization of the product form a mixture of ethyl ether and ethanol, hence providing a not crystalline solid with two DSC peaks respectively at 114° C. and 188° C., although the starting material used for the reworking example was quite a pure substance (HPLC Analysis (A/A %) is 98.95% of Enclomiphene), and having a substantially the same chemical purity of that used in the prior art experiment (m.p. of our Enclomiphene BPA salt was 218° C. versus 220-222° C. of the prior art Enclomiphene BPA salt of Example 31).

The U.S. Pat. No. 2,914,563, in example 3, discloses a process for the preparation of trans-Clomiphene citrate, containing from 30% to 50% of cis-Clomiphene, as citrate, by reaction of 1-p-(β-diethylaminoethoxy)phenyl]-1,2-diphenylethylene hydrochloride with N-chlorosuccinimmide in dry chloroform under reflux.

Khimiko-Farmatsevticheskii Zhurnal (1984), 18(11), 1318-24 English translation in the review *Pharmaceutical Chemistry Journal* November 1984, Volume 18, Issue 11, pag. 758-764 (Title: Synthesis and biological study of the cis- and trans-isomers of Clomiphene citrate and some intermediates of its synthesis) discloses the trans-isomer of Clomiphene citrate, i.e. Enclomiphene citrate, characterized by:

$^1$H-NMR (MeOD) d 7.4-6.7 (m, 14H); 4.27 (t, 2H, —OCH$_2$); 3.51 (t, 2H, CH$_2$—N); 3.28 (q, 4H, 2×N—CH$_2$)); 2.73 (2H); 2.78 (2H); 1.31 (t, 6H, 2×N—C—CH$_3$)) Melting point: 138-139° C. (98% purity by GLC);

IR spectrum, v cm$^{-1}$ (suspension in mineral oil): 3640, 3430, 1720, 1710 (citrate), 1600-1555 (broad band, stilbene system); 750.

UV spectrum: Å max=243 nm, ε 21,800 and Å max 300 nm, ε 11,400.

These prior art methods for the preparation of Enclomiphene citrate do not allow the preparation of Enclomiphene citrate having needle shaped crystal habit, indeed the crystallization by means of a mixture of ethyl ether and ethanol does not provide a crystalline solid having needle crystals.

Moreover, Enclomiphene citrate was described in literature with different melting points, in particular, 133-135° C. and 138-139° C. Said solid forms of Enclomiphene citrate fail to comply with stabilities studies and furthermore show relatively poor solubility in water either in neutral or acid pH.

Furthermore, the prior art methods have the drawbacks related to the poor reproducibility of the process and of the solid form thus obtained.

SUMMARY OF INVENTION

The problem addressed by the present invention is therefore that of providing a process for the preparation of Enclomiphene citrate having needle shaped crystal habit, by means of a reproducible process.

This problem is solved by a process for the preparation of Enclomiphene citrate as outlined in the annexed claims, whose definitions are integral part of the present description.

Particularly, the present invention provides a process for the preparation of Enclomiphene citrate of formula (I):

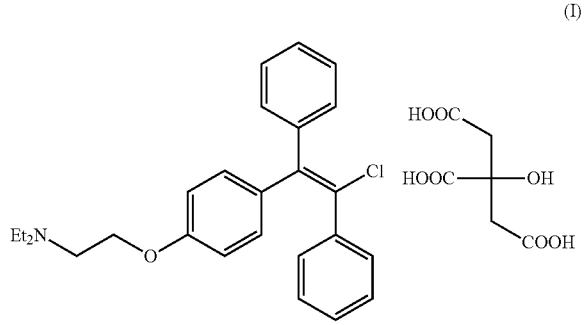

(I)

having needle shaped crystal habit, by means of crystallization of Enclomiphene citrate of formula (I) with a mixture of a C2-C5 alkyl alcohol and water, wherein the amount of water is comprised between 10% and 40% v/v.

As a further aspect, the process provides an improved solid form of Enclomiphene citrate, said form being Enclomiphene citrate having needle shaped crystal habit which shows the following properties:
- is thermodynamically more stable,
- complies with the stabilities studies under thermal/humidity conditions,
- is more soluble in water neutral or at acid pH values, furthermore,
- and/or is in form of only needle crystals and is an homogeneous solid,
- and/or has a specific particle size distribution.

As another aspect, it is provided Enclomiphene citrate micronized having a specific mean particle size, which is comprised in the range between 3 and 25 microns.

As further aspect, it is provided a process for the preparation of Enclomiphene citrate of formula (I) having an amount of Z-isomer less of 0.20 A/A %.

Further features and advantages of the processes and solid forms according to the invention will result from the description hereafter reported of examples of realization of the invention, provided as an indication of the invention.

DESCRIPTION OF EMBODIMENTS

The present invention is related to a process for the preparation of Enclomiphene citrate of formula (I):

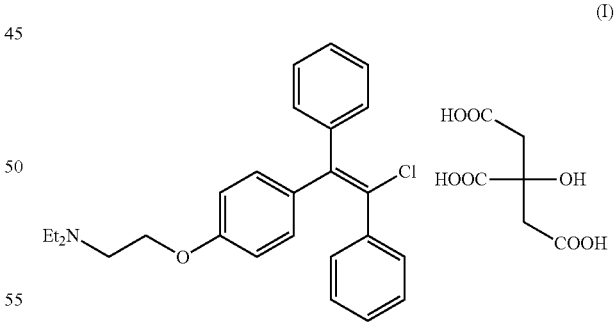

(I)

having needle shaped crystal habit, by means of crystallization of Enclomiphene citrate of formula (I) with a mixture of a C2-C5 alkyl alcohol and water, wherein the amount of water is comprised between 10% and 40% v/v.

It has been indeed surprisingly found that the crystallization Enclomiphene citrate of formula (I), with a mixture of a C2-C5 alkyl alcohol and water, wherein the amount of water is comprised between 10% and 40% v/v, is a well reproducible and solid process for obtaining Enclomiphene citrate having needle shaped crystal habit.

As a further advantage of the process of the present invention, it is pointed out that the process provides an Enclomiphene citrate having needle crystals with a big size and/or length, specifically, having mean square weight is comprised in the range from 60 μm to 120 μm.

Another further advantage of the process of the present invention is that it allows the production of Enclomiphene citrate having needle shaped crystal habit in the form of only needle crystals. The process of the present invention indeed provides Enclomiphene citrate having needle shaped crystal habit which is an homogeneous solid.

Figure 2:
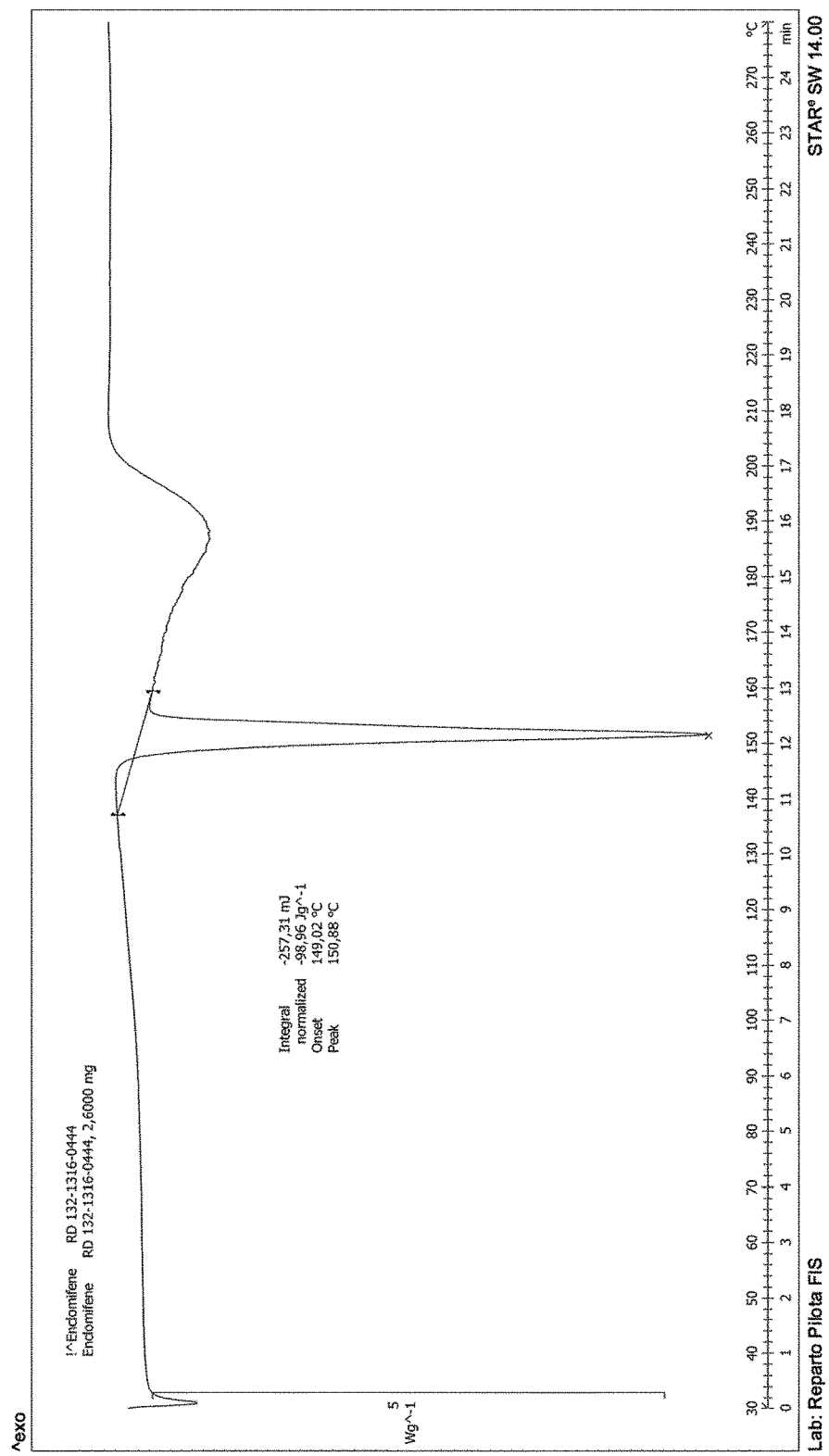
FIG. 2 shows the DSC curve of the solid form of Enclomiphene citrate having needle crystal habit obtained by crystallization from a mixture of ethanol and 15% v/v water.
Figure 3:
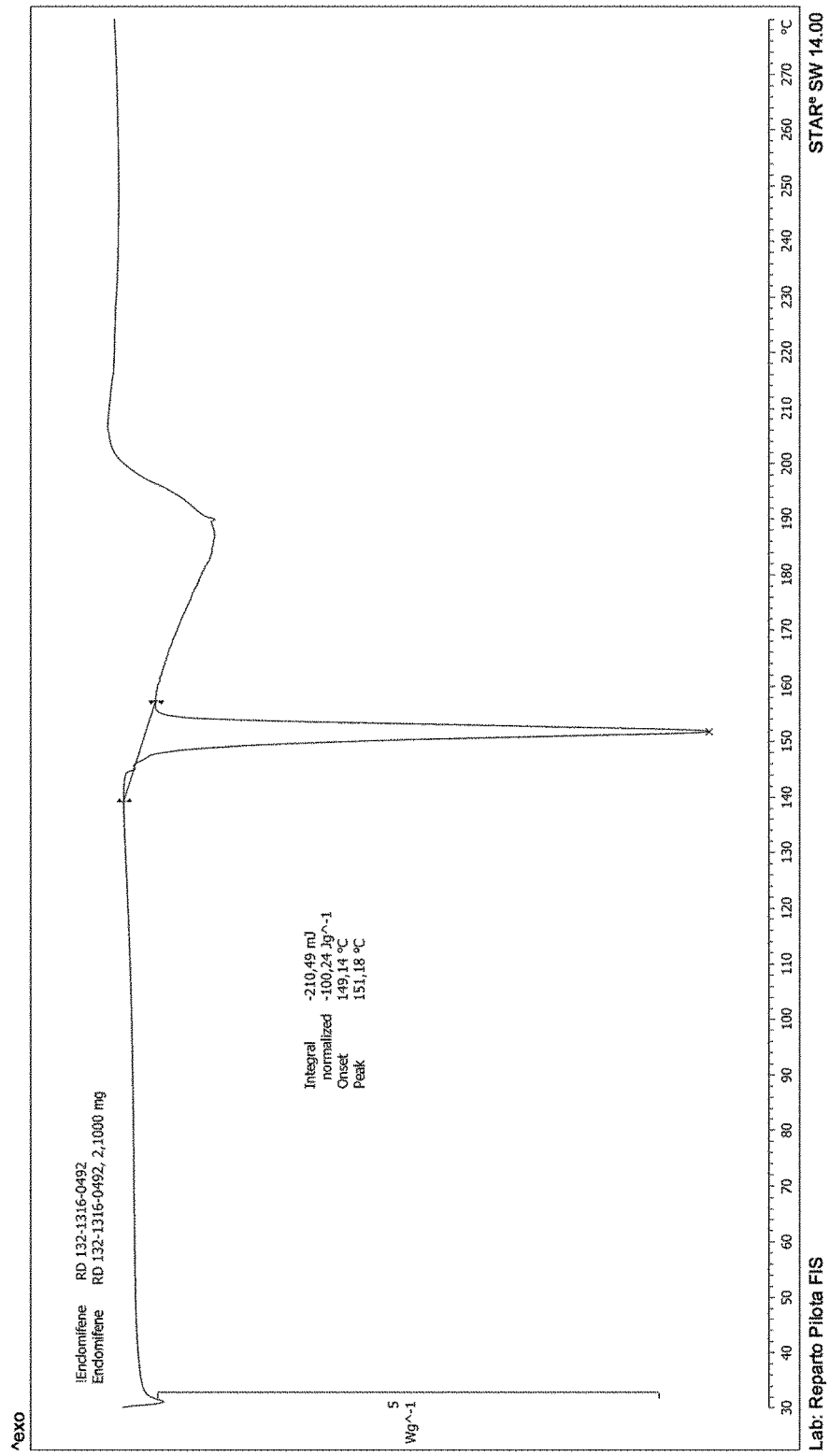
FIG. 3 shows the DSC curve of the solid form of Enclomiphene citrate having needle crystal habit obtained by crystallization from a mixture of isopropanol and 15% v/v water.
Figure 4:
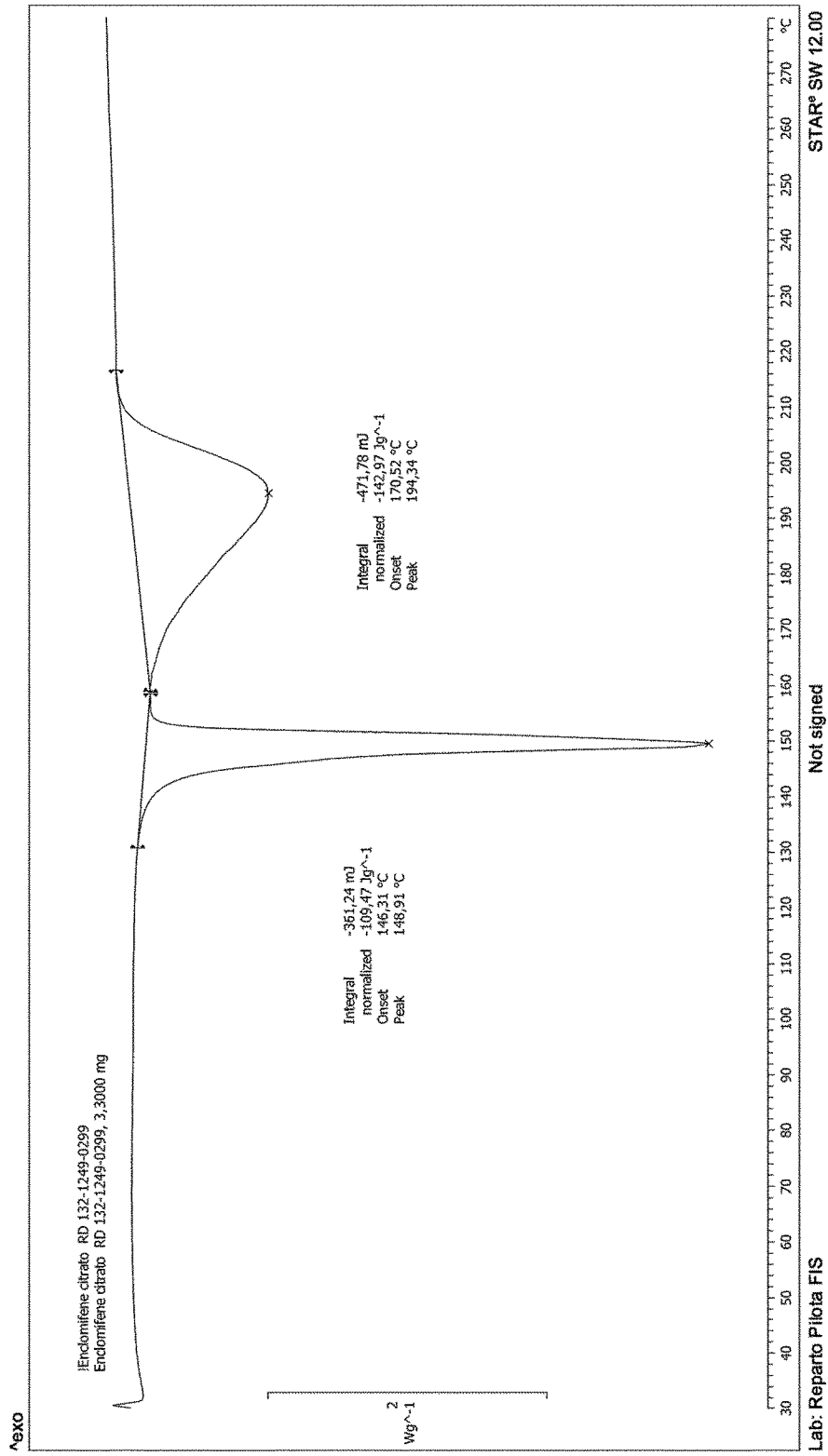
FIG. 4 shows the DSC curve of the solid form of Enclomiphene citrate having non-needle crystal habit obtained by crystallization from a mixture of acetone and 15% v/v water.
Figure 9:
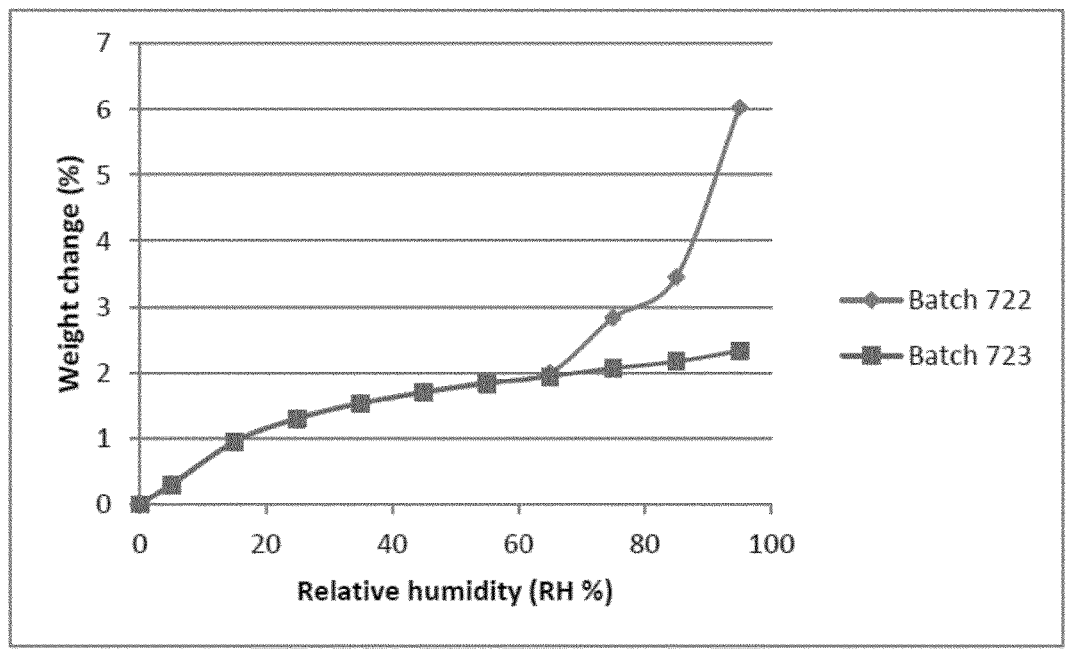
FIG. 9 shows the sorption isotherm comparison of batch 722, i.e. Enclomiphene citrate having non-needle crystals, as crystallized from acetone, and batch 723, i.e. Enclomiphene citrate having needle crystals, crystallized from ethanol.

Moreover, another important advantage concerning Enclomiphene citrate having needle crystals obtained by the process of the present invention, is that said solid form has the highest thermal stability, as confirmed by the stabilities studies under thermal/humidity conditions as shown by FIG. 9, and as described in example 11, and also by the highest melting point as shown in FIG. 2 and FIG. 3, in comparison with FIG. 4.

Finally, a further relevant aspect of the Enclomiphene citrate having needle shaped crystal habit, produced according the process of the present invention, is its solubility, in particular said solid form is more soluble in water neutral or at acid pH values compared with Enclomiphene citrate having non-needle shaped crystal habit. Said solubility studies give the indication that Enclomiphene citrate having needle shaped crystal habit has higher bioavailability.

The process of the present invention provides Enclomiphene citrate of formula (I), which is also named Enclomiphene monocitrate; specifically the terms citrate or monocitrate means 1 mole of citric acid for 1 mole of Enclomiphene.

The process of the present invention is carried out by means of a crystallization of Enclomiphene citrate of formula (I). The crystallization, in the present case, is a process of formation of solid crystals from a solution wherein Enclomiphene citrate of formula (I) has been previously prepared and/or solubilized. In particular the term crystallization of the process of the present invention means either crystallization or recrystallization.

The recrystallization is a technique used for purifying chemical compounds and/or for obtaining a different solid forms (e.g. polymorphs), in particular a solid compound is solubilized in an appropriate solvent, and then the compound re-become a solid, typically a solid crystal, by means of heating and then cooling treatment or by solubilisation in a proper solvent and addition of an anti-solvent.

The process of the present invention can be thus, for example, carried out starting from Enclomiphene citrate and recrystallizing it by heating/cooling treatment or, alternatively, can be carried out by obtaining Enclomiphene citrate in solution and then crystallizing the product, for example, by cooling or by addition of an anti-solvent, or by other ways.

According the process of the present invention the crystallization of Enclomiphene citrate of formula (I) is carried out with a mixture of a C2-C5 alkyl alcohol and water, wherein the amount of water is comprised between 10% and 40% v/v.

A mixture of a C2-C5 alkyl alcohol and water, wherein the amount of water is comprised between 10% and 40% v/v, means that the volume of water is form 10% to 40% of the entire volume of the solvent mixture. For example, 1 Liter of a mixture of ethanol and 10% v/v of water means 900 mL of ethanol and 100 mL of water. Again, 10 mL of a mixture of isopropanol and 40% v/v of water means 6 ml of isopropanol mixed with 4 ml of water.

According to a preferred embodiment of the process of the present invention, the term C2-C5 alkyl alcohol, a component of the above mentioned mixture, means one alkyl alcohol selected in the group comprising: absolute ethanol, ethanol; isopropanol or 2-propanol; 1-propanol; 1-Butanol; 2-Butanol; 2-Propanol, 2-methyl-; 1-Propanol, 2-methyl-; 1-Pentanol; 1-Butanol, 3-methyl-; 1-Butanol, 2-methyl-; 2-Butanol, 2-methyl-; 2-Pentanol; 3-Pentanol; 1-Propanol, 2,2-dimethyl-; 2-Butanol, 3-methyl-.

According to a more preferred embodiment of the process of the present invention, the C2-C5 alkyl alcohol is ethanol or isopropanol.

Figure 5:
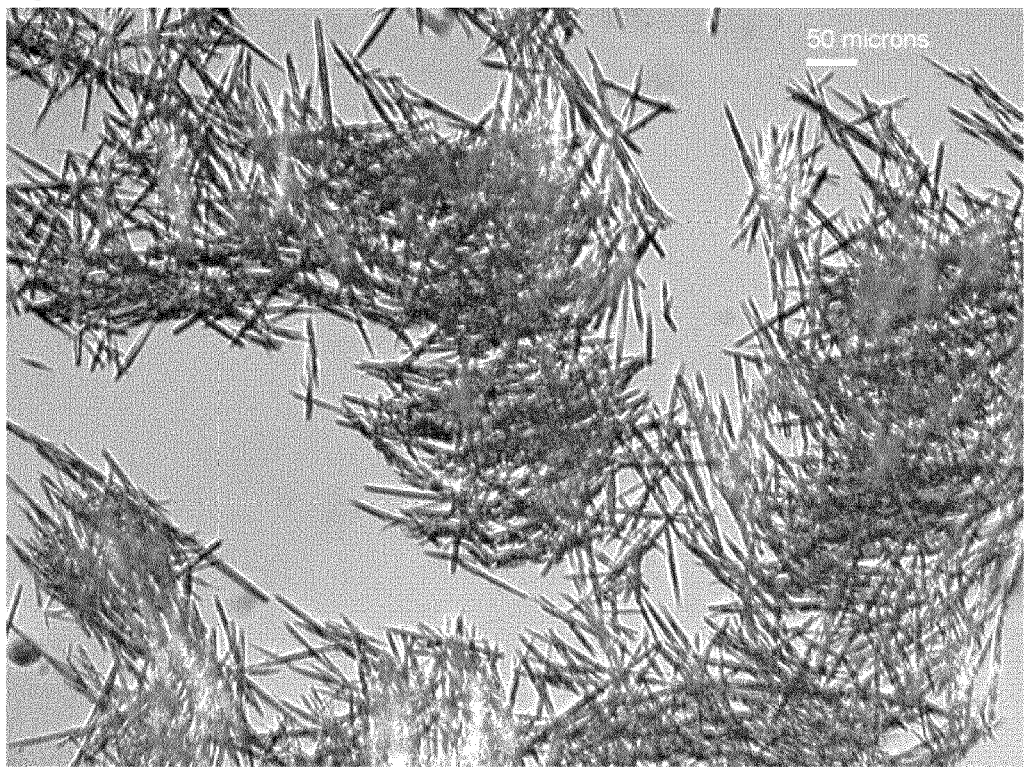
FIG. 5 shows microscopy analysis, i.e. a picture with scale 50 μm (size of 50 μm in the upper side of the picture), of the crystals of Enclomiphene citrate, having needle shaped crystal habit, obtained by crystallization from a mixture of ethanol and 30% v/v water.
Figure 6:
FIG. 6 shows microscopy analysis, i.e. a picture with scale 50 μm (size of 50 μm in the upper side of the picture), of the crystals of Enclomiphene citrate, having needle shaped crystal habit, obtained by crystallization from a mixture of n-propanol and 15% v/v water.
Figure 7:
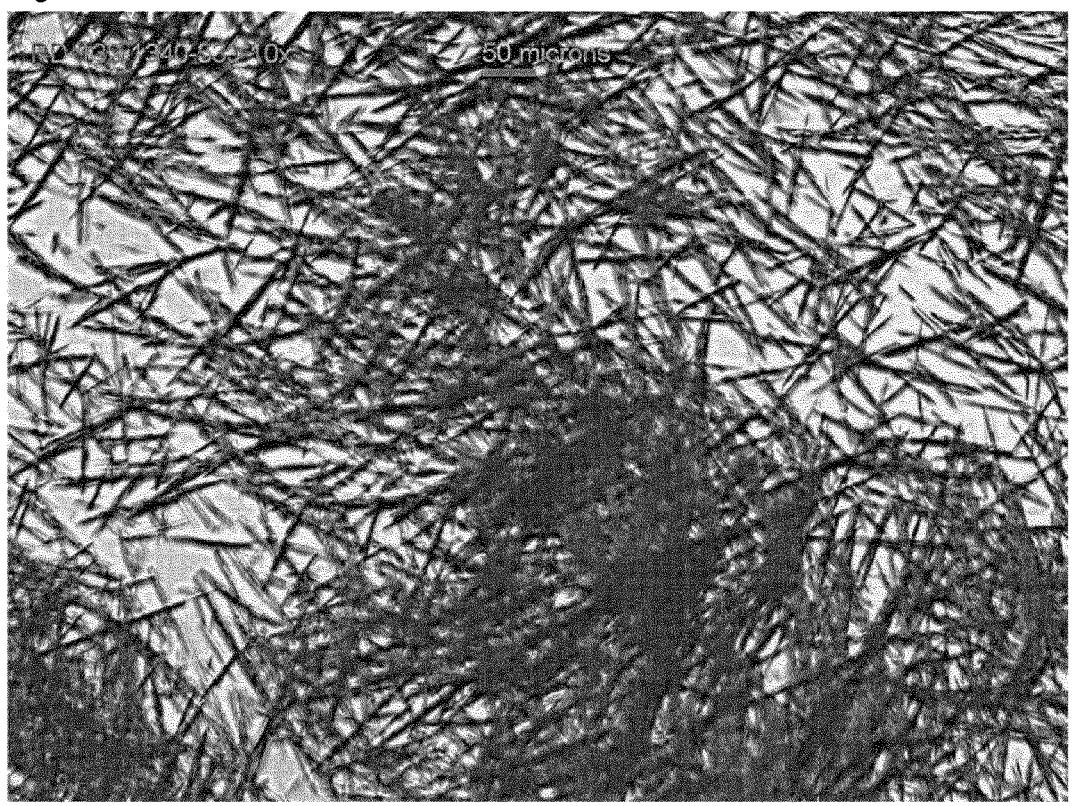
FIG. 7 shows microscopy analysis, i.e. a picture with scale 50 μm (size of 50 μm in the upper side of the picture), of the crystals of Enclomiphene citrate, having needle shaped crystal habit, obtained by crystallization from a mixture of n-butanol and 15% v/v water.
Figure 8:
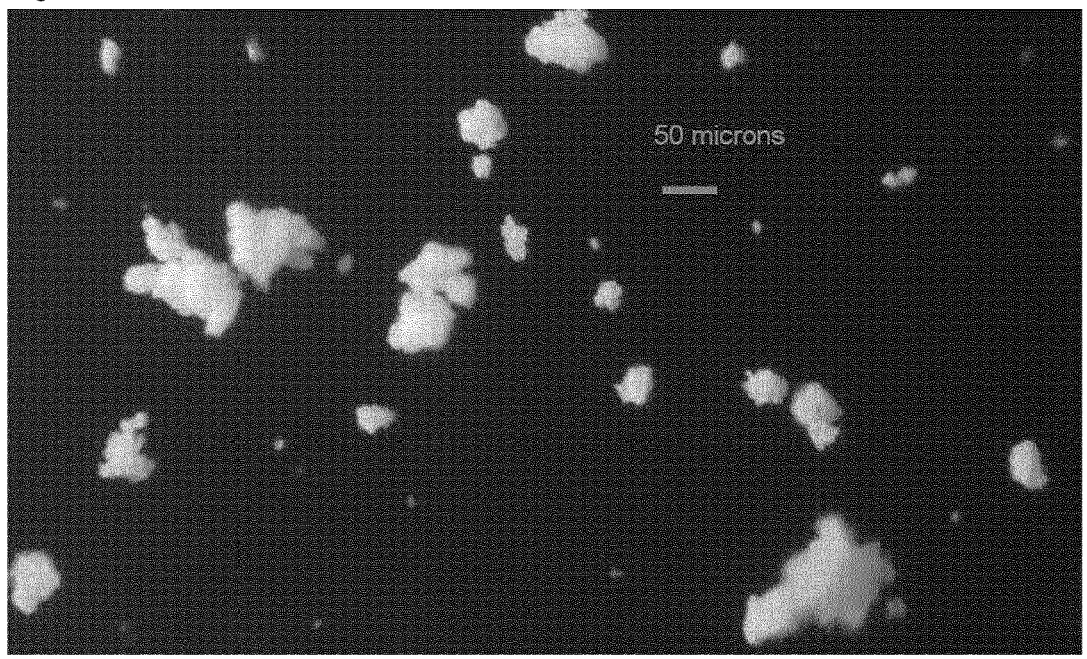
FIG. 8 shows microscopy analysis, i.e. a picture with scale 50 μm (size of 50 μm in the upper side of the picture), of Enclomiphene citrate, having non-needle crystals, obtained by crystallization from a mixture of acetone and 15% v/v water.

The example 6 provides a clear comparative evidence of the effect of the present invention, indeed, Enclomiphene citrate of formula (I) prepared by means of crystallization of Enclomiphene citrate of formula (I) with a mixture of a acetone and 15% v/v of water, has not needle crystal, since it clearly has different crystal morphology (see FIG. 8 versus FIGS. 5, 6 and 7).

The different crystal habit of the two solid forms, one obtained crystallizing with a mixture of a acetone and 15% v/v of water (non-needle crystals) and the other with a mixture of an ethanol and 15% v/v of water (needle crystals) was indeed well evident by microscopy analysis.

In particular, the comparison of pictures in FIG. 8 and FIGS. 5, 6 and 7 acquired by microscopy analysis provides a better further evidence of the different crystal habit of the two forms.

Moreover, FIG. 5-7 clearly show the needle crystal habit of Enclomiphene citrate obtained by means of crystallization of Enclomiphene citrate of formula (I) with a mixture of a C2-C5 alkyl alcohol and water, wherein the amount of water is comprised between 10% and 40% v/v.

Specifically, a crystal having needle shape, i.e. a needle crystal, is a thin, cylindrical crystal, often, but not necessarily, with a sharp point on the end.

According to a preferred embodiment of the process of the present invention, the amount of water in the mixture of a C2-C5 alkyl alcohol and water is comprised between 10% and 30% v/v.

According to a more preferred embodiment of the process of the present invention, the amount of water in the mixture of a C2-C5 alkyl alcohol and water is comprised between 12% and 20% v/v.

According to an again more preferred embodiment of the process of the present invention, the amount of water in the mixture of a C2-C5 alkyl alcohol and water is 15% v/v.

According to a preferred embodiment of the process of the present invention, the crystallization of Enclomiphene citrate of formula (I) is carried out in a mixture is of ethanol or isopropanol and water, wherein the amount of water is comprised between 10% and 30% v/v.

According to a preferred embodiment of the process of the present invention, the crystallization of Enclomiphene citrate of formula (I) is carried out in a mixture is of ethanol or isopropanol and water, wherein the amount of water is comprised between 12% and 20% v/v.

According to a more preferred embodiment of the process of the present invention, the crystallization of Enclomiphene citrate of formula (I) is carried out in a mixture is of ethanol or isopropanol and water, wherein the amount of water is 15% v/v.

According to a preferred embodiment of the process of the present invention, the crystallization of Enclomiphene citrate of formula (I) is carried out in the amount of mixture of a C2-C5 alkyl alcohol and water, that is comprised between 10 and 15 volumes referred to the amount of Enclomiphene citrate (I).

The above mentioned volumes of the mixture of a C2-C5 alkyl alcohol and water are referred to the amount of Enclomiphene citrate (I). The amount of Enclomiphene citrate can be the weight of the starting material Enclomiphene citrate or can be determined by stoichiometric calculations assuming that all the Enchlomiphene is transformed in Enclomiphene citrate.

Volumes means volume of solvent per unit of product being the weight of Enclomiphene citrate. Thus, for example, 1 volume is 1 Liter per 1 Kilo, or 1 mL for 1 gram, or 1 microliter per 1 milligram. Thus, 10 volumes means for example 10 microliters per 1 milligram of substance, in this case, the compound of formula (I).

The process of the present invention can be carried out at a temperature comprised between 20° C. and 100° C.

According to a preferred embodiment of the process of the present invention, the crystallization of Enclomiphene citrate of formula (I) is carried out at the temperature of beginning of the crystallization, that is comprised between 60° C. and 70° C.

According to a more preferred embodiment of the process of the present invention, the crystallization of Enclomiphene citrate of formula (I) is carried out at the temperature of beginning of the crystallization of 65° C.

According to a preferred embodiment of the process of the present invention, the temperature during the crystallization of Enclomiphene citrate of formula (I) decreases from a temperature in the range from 60° C. to 70° C. to the temperature of 0° C. in 3 hours.

The temperature cooling ramp is stepwise: initial slow cooling and then a gradually faster cooling until 0° C., in particular said cooling down is carried out as described in the following steps (see also FIG. 10):

from a temperature of 65° C. to 60° C. is reached in amount of time of 80 minutes,
from a temperature of 60° C. to 55° C. is reached in amount of time of 50 minutes,
from a temperature of 55° C. to 30° C. is reached in amount of time of 30 minutes,
from a temperature of 30° C. to 0° C. is reached in amount of time of 30 minutes.

According to a preferred embodiment of the process of the present invention, the crystallization of Enclomiphene citrate of formula (I), with a mixture of a C2-C5 alkyl alcohol and water, wherein the amount of water is comprised between 10% and 40% v/v, is seeded at a temperature comprised between 60° C. and 55° C. with Enclomiphene citrate of formula (I) having needle shaped crystal.

The seed of Enclomiphene citrate of formula (I) having needle shaped crystal is an amount from 0.20% w/w to 0.50% w/w referred to the entire amount of Enclomiphene citrate (I).

The compound Enclomiphene citrate can be obtained with various methods, for example dissolving Enclomiphene of formula (II) in a mixture of C2-C5 alkyl alcohol and water, wherein the amount of water is comprised between 10% and 40% v/v, thus obtaining a solution of Enclomiphene of formula (II), and then adding citric acid or citric acid monohydrate.

Alternatively, Enclomiphene citrate is formed by converting solid Enclomiphene BPA salt to Enclomiphene of formula (II) in a solution and then adding monohydrate or anhydrous citric acid. Said addition of citric acid can be as solid form or in solution of a mixture of a C2-C5 alkyl alcohol and from 10% to 40% v/v of water.

Furthermore, the amount of adding of citric acid is comprised in a range from 0.97 to 1.12 molar equivalents, preferably in a range from 1.00 to 1.10 molar equivalents.

A solution of Enclomiphene of formula (II) can be prepared dissolving a solid form of Enclomiphene of formula (II) in a solvent; or can be prepared converting a solid form of Enclomiphene BPA salt to Enclomiphene of formula (II) in a solution.

According to a preferred embodiment of the process of the present invention, Enclomiphene citrate of formula (I) is prepared by addition of solid citric acid or citric acid monohydrate to a solution of Enclomiphene of formula (II), in a mixture of C2-C5 alkyl alcohol and from 10% to 40% v/v of water.

According to a more preferred embodiment of the process of the present invention, Enclomiphene citrate of formula (I) is prepared by addition of citric acid or citric acid monohydrate to a solution of Enclomiphene of formula (II), wherein both Enclomiphene and said citric acid are solubilized into a mixture of a C2-C5 alkyl alcohol and water, wherein the amount of water is comprised between 10% and 40% v/v.

According to a more preferred embodiment of the process of the present invention, the solution of Enclomiphene of formula (II) and the solution, wherein the citric acid is solubilized, are the same solution that is a mixture of a C2-C5 alkyl alcohol and water, wherein the amount of water is comprised between 10% and 40% v/v.

Specifically, the above mentioned mixture of a C2-C5 alkyl alcohol and water is the same for both the solution of Enclomiphene of formula (II) and the solution containing the citric acid.

According to another preferred embodiment of the process of the present invention, the amount of mixture of a C2-C5 alkyl alcohol and water, wherein the amount of water is comprised between 10% and 40% v/v, it is comprised between 5 and 6 volumes referred to the amount of Enclomiphene citrate (I).

The above mentioned volumes of the mixture of a C2-C5 alkyl alcohol and water of solution of Enclomiphene of formula (II) are referred to the amount of Enclomiphene citrate (I) which can be the weight of the starting material or can be determined by stoichiometric calculations assuming that all the Enchlomiphene of formula (II) is transformed in Enclomiphene citrate (I).

According to a preferred embodiment of the process of the present invention, the crystallization of Enclomiphene citrate of formula (I) is performed by addition of citric acid to a solution of Enclomiphene of formula (II), said addition of citric acid is carried out at a temperature comprised between 60° C. and 70° C.

The molar yield of the process according to the present invention starting from Enclomiphene of formula (II) is comprised between 90% and 96%.

According to a preferred embodiment of the invention, the process comprises the further steps:

a) conversion of the starting material Enclomiphene BPA salt of formula (III):

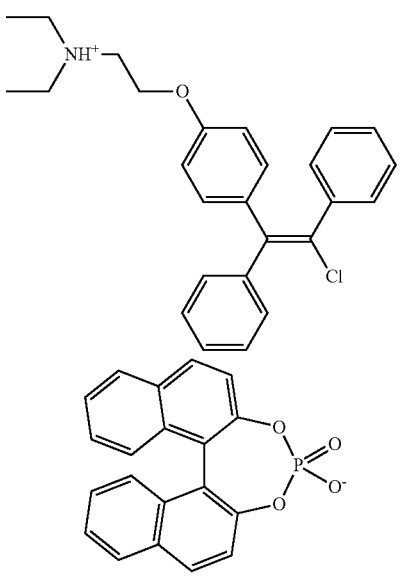

to Enclomiphene of formula (II):

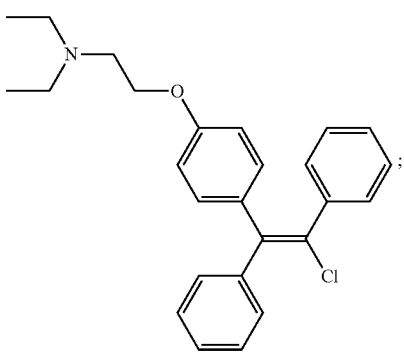

b) conversion of Enclomiphene of formula (II) obtained in step a) to Enclomiphene citrate of formula (I).

Enchlomiphene BPA salt can be prepared by addition of BPA racemic acid to a solution of Clomiphene in a solvent. BPA racemic acid is racemic binaphthyl-phosphoric acid, i.e. the (±)-1,1'-Binaphthyl-2,2'-diyl hydrogenphosphate.

Alternatively, Enchlomiphene BPA salt is prepared by addition of chiral BPA to a solution of Clomiphene in a solvent. Chiral BPA, i.e., single enantiomer of the binaphthyl-phosphoric acid, i.e. the (+)-1,1'-Binaphthyl-2,2'-diyl hydrogenphosphate or (+1,1'-Binaphthyl-2,2'-diyl hydrogenphosphate, can be added to a solution of Clomiphene achieving substantially the same results obtained using the BPA racemic form. The process wherein BPA acid is racemic is preferred since it is the one economically more advantageous.

The Enclomiphene BPA salt of formula (III) can be converted to Enclomiphene of formula (II) in the step a), for example, by suspending of Enclomiphene BPA salt (III), in methyl-tert-butyl ether (MTBE), isopropanol (IPA) and water, and adding an ammonia solution 30 wt % thus obtaining Enclomiphene of formula (II).

Then, after the removal of MTBE by slight distillation, the conversion of the compound of Enclomiphene of formula (II) obtained in step a) to Enclomiphene citrate of formula (I) is carried out by addition of citric acid to the solution of Enclomiphene of formula (II) in a mixture of an C2-C5 alkyl alcohol and from 10% to 40% v/v of water.

According to a preferred embodiment of the process of the invention, Enclomiphene of formula (II) obtained in step a) is not isolated as solid.

Specifically, the process of the invention can be carried out one-pot, i.e. starting from step a) and continuing to step b), thus producing a solid Enclomiphene citrate of formula (I), keeping the compound of Enclomiphene of formula (II) obtained in step a) in a solution, i.e. without isolating it in a solid form.

According to a preferred embodiment, the process of the invention comprises a further step of purification of the Enclomiphene BPA salt of formula (III) through the recrystallization of Enclomiphene BPA salt of formula (III) or through the conversion of said salt to Enclomiphene of formula (II) and then re-preparing Enclomiphene BPA salt of formula (III).

Said further step of purification of the Enclomiphene BPA salt of formula (III) can be carried out through the recrystallization of Enclomiphene BPA salt of formula (III) by heating/cooling treatment or by addition of an anti-solvent. In particular, a solid form of Enclomiphene BPA salt of formula (III) is dissolved in a solution of dimethylformamide (DMF) and methanol at high temperature. Then, after the addition of an anti-solvent, i.e. methanol, said solution is cooled down, thus obtaining a purified Enclomiphene BPA salt of formula (III).

Alternatively, the Enclomiphene BPA salt of formula (III) can be purified through the conversion of Enclomiphene BPA salt of formula (III) to Enclomiphene of formula (II), and then re-preparing the Enclomiphene BPA salt of formula (III).

Enclomiphene BPA salt of formula (III) can be purified through the conversion of Enclomiphene BPA salt of formula (III) to Enclomiphene of formula (II), which can be isolated or non-isolated, in the latter case, thus remaining in solution.

According to the preferred embodiment of the present invention, the conversion of Enclomiphene BPA salt of formula (III) to Enclomiphene of formula (II) is carried out in methyl-tert-butyl ether (MTBE), isopropanol (IPA) and water, and later by addition of an ammonia solution, for obtaining Enclomiphene of formula (II), which is not isolated as solid.

Successively, the re-preparation the Enclomiphene BPA salt of formula (III) is carried out by addition of racemic binaphthyl-phosphoric acid to the beforehand prepared Enclomiphene of formula (II) in an organic solvent, i.e. methanol, thus finally obtaining a purified Enclomiphene BPA salt of formula (III). Enclomiphene BPA salt, purified according to the above mentioned embodiment, contains less than 0.15% (HPLC A/A % of the Cis-Clomiphene).

The process of the invention provides Enclomiphene citrate of formula (I) having needle shaped crystal habit. In particular, the process of the present invention provides Enclomiphene citrate of formula (I) having needle shaped crystal habit which has mean square weight comprised in the range from 60 μm to 120 μm and/or which is in the form of only needle crystals.

The mean square weight means is determined by chord-length distribution analysis of Enclomiphene citrate of formula (I), in particular, was through a PVM probe.

The process of the present invention provides advantageously an Enclomiphene citrate having needle crystals with a big size and/or length, specifically the particle size distribution comprised in the range from 60 μm to 120 μm as determined by chord-length distribution analysis.

The molar yield of the process according to the present invention, having as starting material Enclomiphene BPA salt, is comprised between 80% and 90%, being typically about 87%.

The process of the present invention provides Enclomiphene citrate of formula (I) having needle shaped crystal habit, i.e. Enclomiphene citrate needle crystals. Said Enclomiphene citrate (I) is also described by the following parameters.

In particular, Enclomiphene citrate having needle shaped crystal habit has a characteristic X-ray powder diffraction pattern with characteristic peaks expressed in 2-Theta values (2θ) at: 5.8, 11.5, each peak ±0.1.

More in particular, Enclomiphene citrate having needle shaped crystal habit has a characteristic X-ray powder diffraction pattern with characteristic peaks expressed in 2-Theta values (2θ) at: 5.8, 11.5, 12.7, 14.9 and 24.9, each peak ±0.1.

Again more particularly, Enclomiphene citrate having needle shaped crystal habit has a characteristic X-ray powder diffraction pattern with characteristic peaks expressed in 2-Theta values (2θ) at: 5.8, 9.7, 10.9, 11.5, 12.7, 14.9, 17.1, 20.6, 21.8, 23.6, 23.7 and 24.9, each peak ±0.1.

The comparison of the DSC curves of FIG. 4 and FIG. 2 provides a clear evidence of the different thermal behavior of the two solid forms of Enclomiphene citrate having two different crystal habits, respectively non-needle and needle crystals, maybe of the same polymorphic form.

The solid form of Enclomiphene citrate having needle shaped crystal habit, obtained by means of crystallization of said Enclomiphene citrate with a mixture of a C2-C5 alkyl alcohol and water, wherein the amount of water is comprised between 10% and 40% v/v, has a melting point of 149° C. as measured by DSC (onset) (See FIG. 2).

Moreover, Enclomiphene citrate having needle shaped crystal habit shows a peak at 151° C. as measured by DSC.

Thus, Enclomiphene citrate having needle shaped crystal habit has a melting point of 149° C. which is higher of that of Enclomiphene citrate having non-needle shaped crystal habit, being 146° C., both measured by DSC (onset) (See respectively FIG. 2 and FIG. 4).

Such a different thermal behavior is also confirmed by the different peak in the DSC analysis: Enclomiphene citrate having needle shaped crystal habit shows a peak at 151° C., an higher temperature compared with the peak at 149° C. of Enclomiphene citrate having non-needle shaped crystal habit.

The above said DSC comparative study give thus evidence that the crystalline habit of Enclomiphene citrate being needle shaped crystals is thermodynamically more stable of the crystal habit being non-needle shaped crystals, since the melting point of the first is higher than that of the latter (151° C. versus 149° C. (peak) and 149° C. versus 146° C. (onset)), and both the forms having higher melting points compared with those disclosed in literature of 133-135° C. and 138-139° C. for Enclomiphene citrate.

It should further noticed that, as discussed above with reference to prior art, the polymorph having crystalline habit non-needle and m.p. of 146° C., should have been identified to be the thermodynamically more stable polymorphic form of Enclomiphene citrate. Nevertheless, Enclomiphene citrate having needle crystals is the solid form having a highest thermal stability. This is confirmed by the highest melting point shown by Enclomiphene citrate having needle crystals.

The higher thermal stability of Enclomiphene citrate having needle crystals was confirmed by comparative stability studies, indeed such a crystal form remains thermodynamically stabile while the solid having crystalline habit non-needle and m.p. of 146° C., after 17 days at room temperature and 95% RH, fails the stability studies. In particular, after 17 and 30 days at room temperature and 95% RH, the intensities of the peaks of the XPRD diffractograms have a very significant drop, respectively to about 50% of the initial intensity and, after 30 days, about 30% of the initial intensity. Said analysis allows to hypothesize an amorphization of a part of the crystal. Such a behavior is in line also with the hygroscopicity study and behavior exemplified in FIG. 9, wherein Enclomiphene having non-needle crystals absorbs relevant amounts of water when exposed at values of humidity higher than 65% RH.

Considering the regulatory requirements to be complied, it is clear that the enhanced thermal stability of Enclomiphene citrate having needle crystals is the key solid form for supplying a product complying with the pharmaceutical requirements related to the stability, including the hygroscopicity behavior.

Enclomiphene citrate having needle crystalline habit, being the thermodynamically more stable solid form, exhibits therefore better storage stability and can be more easily formulated into pharmaceutical compositions of medicaments.

The higher thermal stability of Enclomiphene citrate having needle shape crystal habit is not the only one advantageous property of such product.

Indeed, Enclomiphene citrate having needle shaped crystal habit, shows a much higher solubility in water, especially in water at pH 4.5, in comparison to Enclomiphene citrate non-needle shaped crystal habit, i.e. Enclomiphene citrate crystallized from a mixture of acetone and 15% v/v water.

In particular, example 10 provides a clear evidence that Enclomiphene citrate having needle shaped crystal habit shows a solubility in water almost double compared with Enclomiphene citrate having non-needle shaped crystal habit, and the solubility at pH 4.5 is four times higher compared with the non-needle shaped crystal habit.

Such solubility study gives the indication that Enclomiphene citrate having needle shaped crystal habit has higher bioavailability compared with Enclomiphene citrate non-needle shaped crystal habit.

Thus, Enclomiphene citrate having needle shaped crystal habit is also suitable for fast-release pharmaceutical composition of Enclomifene citrate.

Moreover, Enclomiphene citrate having needle shaped crystal habit, shows much better hygroscopicity behavior, especially in comparison to Enclomiphene citrate having non-needle shaped crystal habit obtained by crystallization form a acetone (see example 11 and FIG. 9).

Another aspect is thus, Enclomiphene citrate of formula (I):

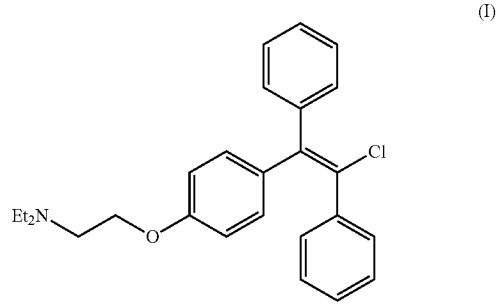

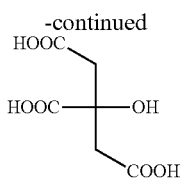

having needle shaped crystal habit, which has a mean square weight comprised in the range from 60 μm to 120 μm.

According to a preferred embodiment, said Enclomiphene citrate has a mean square weight comprised in the range from 80 μm to 100 μm.

The needle crystals of Enclomiphene citrate of formula (I) obtained by the process of the present invention are particularly big by size and/or length. Indeed, the length of said Enclomiphene citrate needle crystals is comprised between 50 and 150 microns, as it is shown in FIGS. 5, 6 and 7.

Furthermore, the length of the most part of Enclomiphene citrate needle crystals obtained by the process of the present invention is comprised between 70 and 130 microns.

Said solid form shows the same advantageous behaviour and in term of thermal stability, hygroscopicity and solubility above described for the needle crystal form (see also example 10 and 11).

According to a preferred embodiment of the present invention, Enclomiphene citrate having needle shaped crystal habit and having a mean square weight comprised in the range from 60 μm to 120 μm is that in it is the form of only needle crystals. Said solid form has the advantage of being an homogeneous solid and therefore is well suitable, especially in terms of processability, for preparing pharmaceutical compositions comprising Enclomiphene citrate.

Another aspect is thus, Enclomiphene citrate of formula (I):

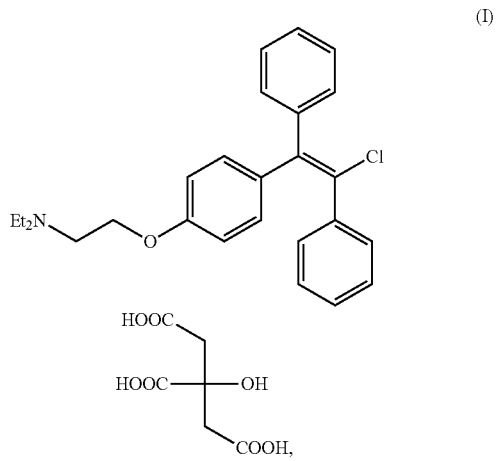

having needle shaped crystal habit wherein said Enclomiphene citrate (I) is in the form of only needle crystals.

Indeed the process of the present invention allows the production of Enclomiphene citrate having needle shaped crystal habit in the form of only needle crystals. It means that said solid form does not contain crystals having different morphology, but contains only needle crystals.

Enclomiphene citrate having needle shaped crystal habit in the form of only needle crystals thus does not contain any soft agglomerate or any other crystal having different morphology.

Moreover, Enclomiphene citrate having needle shaped crystal habit is an homogeneous solid.

Enclomiphene citrate having needle shaped crystal habit and which is in the form of only needle crystals can be suitably employed for the preparation of pharmaceutical compositions.

According to a preferred embodiment, said Enclomiphene citrate (I), having needle shaped crystal habit and being in the form of only needle crystals, has mean square weight comprised in the range from 60 μm to 120 μm.

According to a more preferred embodiment, the said Enclomiphene citrate (I) has a mean square weight comprised in the range from 80 μm to 100 μm.

According to another preferred embodiment, Enclomiphene citrate (I) having needle shaped crystal habit and being in the form of only needle crystals, has a mean particle size comprised in the range between 3 and 25 microns.

A mean particle size means the measure relates to mean diameter of the as determined by laser diffraction.

Also said solid form shows the same advantageous behaviour and in term of thermal stability, hygroscopicity and solubility above described for the needle crystal form (see also example 10 and 11).

Another object of the present in invention are pharmaceutical compositions comprising Enclomiphene citrate of formula (I) in form and only needle crystals and one or more pharmaceutical acceptable excipients Examples of suitable pharmaceutical compositions comprising Enclomiphene citrate according to the present invention are those disclosed in WO2006102232A2, WO2010054248A1, WO2013020017A1, WO2013123218A1 or WO2013130832A1 with the difference that Enclomiphene citrate having needle shaped crystal habit is used instead of the disclosed Enclomiphene having non-needle shaped crystal habit.

Pharmaceutical compositions have different dosage forms, which may include, for example, capsules, tablets, powders, suspensions or any other suitable dosage form. In such said dosage forms, the Enclomiphene citrate (I) having needle shaped crystal habit may be combined with one or more pharmaceutically acceptable excipients, carriers or diluents, such as, for example mannitol, silicic derivatives or sugar.

Enclomiphene citrate of formula (I) having needle shaped crystal habit, obtained by means of crystallization of Enclomiphene citrate of formula (I) with a mixture of a C2-C5 alkyl alcohol and water, wherein the amount of water is comprised between 10% and 40% v/v, as above described, or the beforehand above mentioned pharmaceutical composition can be used in medicine.

Enclomiphene citrate of formula (I) needle crystal or the above mentioned pharmaceutical composition can be used for the treatment of secondary hypergonadism and the type 2 diabetes.

In particular, Enclomiphene citrate having needle shaped crystal habit can be used in the treatment ovulatory dysfunction or polycystic ovary syndrome.

The process of the present invention can comprise a further step of micronization, which is optional.

As another aspect, Enclomiphene citrate of formula (I):

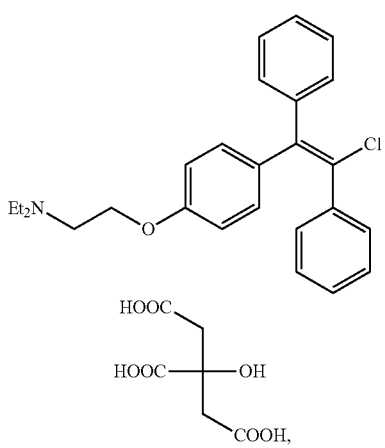

(I)

in micronized form for providing advantageous pharmaceutical effects in the therapy.

The term micronized Enclomiphene citrate of formula (I) means Enclomiphene citrate having a mean particle size comprised in the range between 3 and 25 microns. Said Enclomiphene citrate (I) can be effectively employed for the preparation of pharmaceutical compositions.

Enclomiphene citrate of formula (I) having a mean particle size comprised in the range between 3 and 25 microns indeed provides pharmaceutical having better bioavailability. According to a preferred embodiment, Enclomiphene citrate has mean particle size comprised in the range between 10 and 20 microns.

According to a preferred embodiment, Enclomiphene citrate having a mean particle size comprised in the range between 3 and 25 microns, or between 10 and 20 microns, has a needle shaped crystal habit. In such a case, especially, where the crystal habit does not facilitates the manufacturing process of the pharmaceutical product, the small particle size distribution provides a very positive effect, thus balancing the two effects, and providing a product which is the more stable solid form of Enclomiphene citrate.

According to a preferred embodiment, Enclomiphene citrate, having a mean particle size comprised in the range between 3 and 25 microns, or between 10 and 20 microns, is in the form of only needle crystals. Such a product is particularly homogenous and therefore appears to be the easiest product to be used in the manufacturing process for preparing the pharmaceutical product. Furthermore it allows a better control of the amount of the active substance dosed during process for preparing the pharmaceutical product, especially with reference to the un-micronized product.

Pharmaceutical composition comprising micronized Enclomiphene citrate of formula (I) and one or more pharmaceutical acceptable excipients can be prepared.

Said pharmaceutical compositions, which contains micronized Enclomiphene citrate of formula (I) can have the same administration route and dosage forms as beforehand described related to pharmaceutical composition comprising un-micronized Enclomiphene citrate of formula (I).

Furthermore, micronized Enclomiphene citrate of formula (I) or the pharmaceutical composition containing said micronized Enclomiphene citrate (I) can be used in medicine, moreover they can be used for the treatment of specific diseases, as beforehand described related to use of Enclomiphene citrate of formula (I).

According to a preferred embodiment, Enclomiphene citrate of formula (I) micronized or the mentioned pharmaceutical composition can be used for the treatment of secondary hypergonadism and the type 2 diabetes.

As another aspect, it is provide a process for the preparation of Enclomiphene citrate of formula (I):

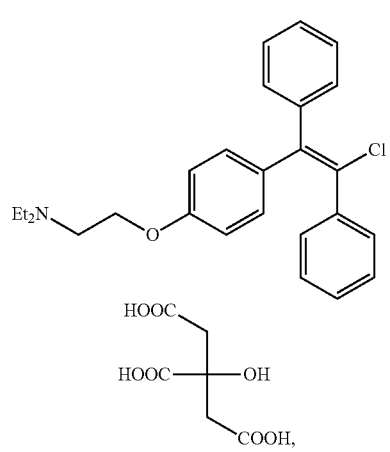

(I)

having an amount of Z-isomer less of 0.20 A/A %, which comprises the following steps:

A) recrystallization of the Enclomiphene BPA salt of formula (III):

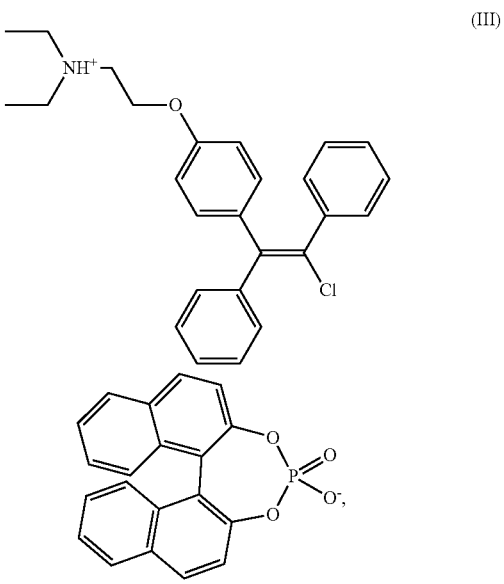

(III)

B) conversion of the recrystallized Enclomiphene BPA salt of formula (III) obtained in step A) to Enclomiphene citrate of formula (I); or comprising the following steps:

1. starting from Enclomiphene BPA salt and obtaining a solution of Enclomiphene of formula (II),
2. adding BPA acid to the solution obtained in the step 1.,
3. isolating Enclomiphene BPA salt of formula (III),
4. conversion of the isolated Enclomiphene BPA salt of formula (III) obtained in step 3. to Enclomiphene citrate of formula (I).

It has been indeed surprisingly found that the above mentioned process allows the preparation of Enclomiphene citrate of formula (I) having a very low amount, less than 0.20% A/A % of Z-isomer impurity of formula (IV):

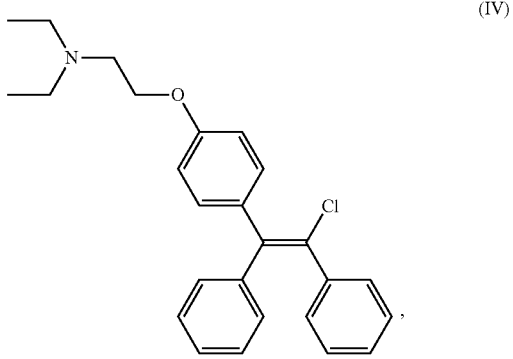 [SMILES: CCN(CC)CCOc1ccc(/C(=C(\Cl)c2ccccc2)c2ccccc2)cc1]

which is also named Z-Clomiphene, it is a typical impurity of the process for the preparation of Enclomiphene citrate of formula (I) which is very difficult to be removed.

Said process for the preparation of Enclomiphene citrate of formula (I), having an amount of Z-isomer less of 0.20 A/A %, is carried out by means of recrystallization of the Enclomiphene BPA salt of formula (III) in step A).

The recrystallization of the step A), is a process of formation of solid Enclomiphene BPA salt of formula (III) from a solution wherein a solid Enclomiphene BPA salt of formula (III) has been previously solubilized. The example 2 is a particular embodiment of said step A).

The above mentioned process can be, for example, thus carried out starting from Enclomiphene BPA salt of formula (III) and recrystallizing it by heating/cooling treatment or, alternatively, obtaining Enclomiphene BPA salt of formula (III) in solution and then crystallizing the product, for example, by cooling or by addition of an anti-solvent, or by other ways.

Said Enclomiphene BPA salt of formula (III) is produced according to various methods for obtaining said compound as beforehand described.

According to a preferred embodiment of the process, the recrystallization of the Enclomiphene BPA salt of formula (III) of the step A) is carried out by a mixture of dimethylformamide (DMF) and a C1-C4 alkyl alcohol.

According to a preferred embodiment of the process, the C1-C4 alkyl alcohol, a component of the above mentioned mixture, means one alkyl alcohol selected in the group comprising: methanol; absolute ethanol; ethanol; isopropanol or 2-propanol 1-propanol; 1-Butanol; 2-Butanol; 2-Propanol, 2-methyl-; 1-Propanol, 2-methyl-.

According to a preferred embodiment of the process, the recrystallization of the Enclomiphene BPA salt of formula (III) of the step A) is carried out by a mixture of dimethylformamide and a C1-C4 alkyl alcohol, wherein a C1-C4 alkyl alcohol is methanol.

According to a preferred embodiment of the process, the recrystallization of the Enclomiphene BPA salt of formula (III) of the step A) is carried out by a mixture of dimethylformamide and a C1-C4 alkyl alcohol, wherein the amount of volumes of dimethylformamide are comprised between 1.5 to 2.5 and the amount of volumes of C1-C4 alkyl alcohol are comprised between 4 to 6, both referred to the amount of Enclomiphene BPA salt of formula (III).

The above mentioned volumes of the mixture of dimethylformamide and a C1-C4 alkyl alcohol are referred to the amount of Enclomiphene BPA salt of formula (III), the amount of Enclomiphene BPA salt can be the weight of the starting material Enclomiphene BPA salt or can be determined by stoichiometric calculations assuming that all the Enclomiphene BPA salt (III) is transformed in Enclomiphene BPA salt of formula (III).

Finally, the conversion in the step B) of the recrystallized Enclomiphene BPA salt of formula (III) obtained in step A) to Enclomiphene citrate of formula (I) can be carried at according to the teaching previously given or according to the example 31 of U.S. Pat. No. 3,848,030.

Alternatively, the process for the preparation of Enclomiphene citrate of formula (I), having an amount of Z-isomer less of 0.20 A/A %, comprises different steps that are disclosed in the previous paragraph.

According to a variant of the process, in the step 1. the starting material BPA salt is treated with a base for giving a solution of Enclomiphene of formula (II).

According to a preferred embodiment of the process, in the step 2. BPA acid is added to the solution obtained in the step 1 for obtaining Enclomiphene BPA salt of formula (III).

In the step 3. Enclomiphene BPA salt of formula (III) is isolated, for example, by filtration or centrifugation.

In the step 4. the isolated Enclomiphene BPA salt of formula (III) obtained in step 3. is converted to Enclomiphene citrate of formula (I); said conversion is carried out as beforehand described.

The last described process for the preparation of Enclomiphene citrate of formula (I), provides an Enclomiphene citrate of formula (I) crystal having different shape crystal habits, for example needle, non-needle, prism, rhomboid, rhombus, rectangle or square crystals.

According to a preferred embodiment of the process the step B) or the step 4. for providing Enclomiphene citrate of formula (I) is carried out with a mixture of a C2-C5 alkyl alcohol and water, wherein the amount of water is comprised between 10% and 40% v/v.

According to a preferred embodiment, the process for the preparation of Enclomiphene citrate of formula (I) provides said compound of formula (I) having an amount of Z-isomer of formula (IV) which is less of 0.10 A/A %.

According to a preferred embodiment, the process for the preparation of Enclomiphene citrate of formula (I) provides said compound of formula (I) having high chemical purity, i.e. more than 99.90% A/A %.

According to a preferred embodiment, the process for the preparation of Enclomiphene citrate of formula (I) provides said compound of formula (I) having high chemical purity, i.e. more than 99.90% A/A % and an amount of Z-isomer of formula (IV) which is less of 0.10 A/A %.

According to a preferred embodiment, the process for the preparation of Enclomiphene citrate of formula (I) provides said compound of formula (I) having needle shaped crystal habit.

According to a preferred embodiment the process, the process for the preparation of Enclomiphene citrate of formula (I) provides said compound of formula (I) which in the form of only needle crystals, said solid being an homogeneous solid.

According to a more preferred embodiment, the process for the preparation of Enclomiphene citrate of formula (I) provides Enclomiphene citrate of formula (I) having an amount of Z-isomer into Enclomiphene citrate which is less of 0.10 A/A % and needle shaped crystal habit.

According to a more particularly preferred embodiment, the process for the preparation of Enclomiphene citrate of formula (I) provides Enclomiphene citrate of formula (I) having an amount of Z-isomer into Enclomiphene citrate which is less of 0.10 A/A %, needle shaped crystal habit and in the form of only needle crystals.

The above mentioned process can comprise a further step of micronization, which is optional.

According to a preferred embodiment, the process for the preparation of Enclomiphene citrate of formula (I) provides Enclomiphene citrate of formula (I) having a mean particle size comprised in the range between 3 and 25 microns.

According to a more preferred embodiment, the processes for the preparation of Enclomiphene citrate of formula (I) provides Enclomiphene citrate of formula (I) having an amount of Z-isomer into Enclomiphene citrate which is less of 0.10 A/A %, needle shaped crystal habit and has a mean particle size comprised in the range between 3 and 25 microns.

According to a more particularly preferred embodiment, the processes for the preparation of Enclomiphene citrate of formula (I) provides Enclomiphene citrate of formula (I) having an amount of Z-isomer into Enclomiphene citrate less of 0.10 A/A %, needle shaped crystal habit, having a mean particle size comprised in the range between 3 and 25 microns and being in the form of only needle crystals.

Moreover, said improved process for the preparation of Enclomiphene citrate having needle shaped crystal allows the preparation of Enclomiphene citrate having high chemical purity, i.e. more than 99.90% by HPLC A/A % with a content of residual cis-Clomiphene impurity lower than 0.10% by HPLC A/A %.

EXPERIMENTAL SECTION

The starting material Clomiphene citrate can be prepared according to well-known prior art methods, or for example, as described in the example 1 of PCT/EP2015/074746 or can be purchased on the market.

Example 1: Preparation of Salt of Enclomiphene with Racemic Binaphthyl-Phosphoric Acid, Starting from Clomiphene Citrate

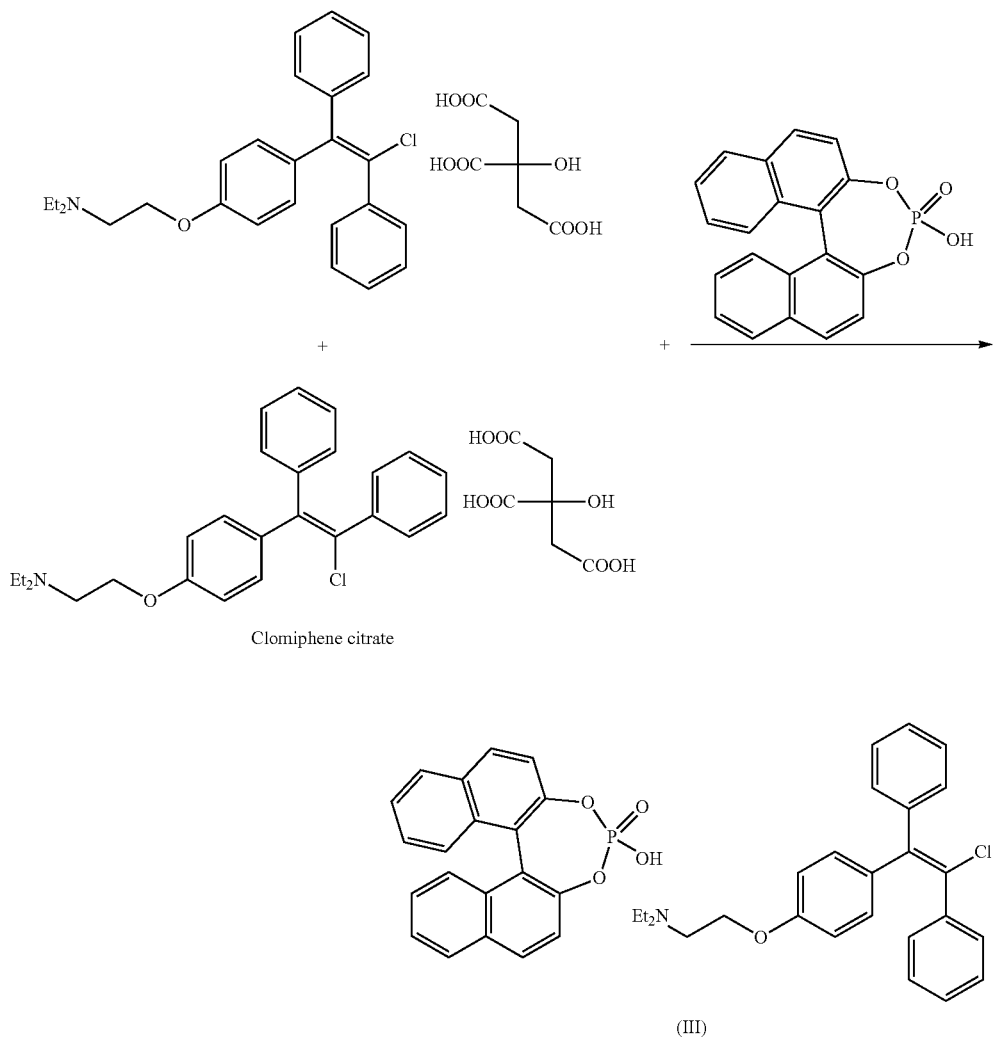

A round bottom flask was charged 100 gr of Clomiphene Citrate (HPLC analysis (A/A %): 65.21% Enclomiphene, 34.06% Z-Clomiphene) and 1000 mL of methanol. The suspension was stirred at 30° C. up the complete dissolution. Then a solution of racemic binaphthyl-phosphoric acid (abbreviated BPA) 30 gr (0.515 eq) in 30 mL of DMF was added. At the end of addition the mixture was stirred for 1 h at 30° C. The obtained suspension was filtered and the solid was washed with 100 mL of methanol.

50.4 gr of Enclomiphene BPA salt (III) were obtained.

HPLC Analysis (A/A %): 97.04% Enchlomiphene, 2.5% Z-Clomiphene.

Example 1b: Preparation of Salt of Enclomiphene with Racemic Binaphthyl-Phosphoric Acid, Starting from Clomiphene Citrate A round bottom flask was charged 50 gr of Clomiphene Citrate and 500 mL of methanol. The suspension was heated at 40-45° C. and stirred up to the complete dissolution. Then a solution of BPA 15 gr (0.515 eq) in 300 mL of methanol was added. At the end of addition the mixture was stirred for 1 h at 20° C. The obtained suspension was filtered and the solid was washed with 100 mL of methanol.

24.1 gr of Enclomiphene BPA salt were obtained.

HPLC Analysis (A/A %): 98.96% Enchlomiphene, 0.69% Z-Clomiphene.

Example 1c: Preparation of Salt of Enclomiphene with Racemic Binaphthyl-Phosphoric Acid, Starting from Clomiphene Citrate In a round bottom flask was charged 100 gr of Clomiphene Citrate and 1000 mL of methanol. The suspension was heated at 40-45° C. and stirred up the complete dissolution. Then a solution of BPA 30 gr (0.515 eq) in 1000 mL of methanol was added. At the end of addition the mixture was stirred for 1 h at 20° C. the obtained suspension was filtered and the solid was wash with 100 mL of methanol.

47.9 gr of Enclomiphene BPA salt were obtained.

HPLC Analysis (A/A %): 98.81% Enclomiphene, 0.79% Z-Clomiphene.

Example 1d: Preparation of Salt of Enclomiphene with Racemic Binaphthyl-Phosphoric, Starting from Clomiphene Citrate In a round bottom flask was charged 150 gr of Clomiphene citrate and 1500 mL of methanol. The suspension was heater at 40-45° C. and stirred up the complete dissolution. Then a solution of BPA 45 gr (0.515 eq) in 900 mL of methanol was added. At the end of addition the mixture was stirred for 1 h at 20° C. the obtained suspension was filtered and the solid was wash with 100 mL of methanol.

76.4 gr of E-Clomiphene BPA salt were obtained.

HPLC Analysis (A/A %): 98.82% Enchlomiphene, 0.80% Z-Clomiphene.

Example 2: Recrystallization of Enclomiphene BPA Salt of Formula (III) (the Step A)

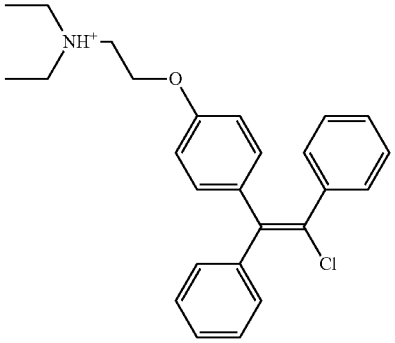

(III)

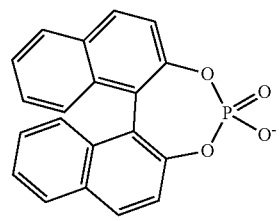

Into a proper 0.5 L reactor, equipped with propeller, temperature probes, condenser; Enclomiphene BPA salt (III) (50 g) and having Z-isomer of 1.64% was suspended in DMF (2.1 L/Kg of Enclomiphene BPA (III)) and methanol (1.4 L/Kg of Enclomiphene BPA salt (III)). The suspension was heated to reflux (~76-79° C.). Further DMF (0.1 L/Kg of Enclomiphene BPA (III)) might be required to improve the solubility of the starting material. Once the starting material was completely dissolved, methanol was added as anti-solvent (3.5 L/Kg of Enclomiphene BPA (III)). The temperature was decreased to 60° C. and the mixture was stirred for 2-3 h. Then, the temperature was further decreased to 20° C. and filtered. The wet cake was washed twice with methanol (1.5 L/Kg of Enclomiphene BPA salt (III)). The product was dried under vacuum at 60-70° C. for 12-24 h. Time of drying could be prolonged until residual DMF is <2500 ppm.

Analysis of quality of the final product of the above mentioned example and of the same product, obtained from repetition following the same process, it is shown in the following table:

| Enclomiphene BPA (III) salt (Starting product) | Enclomiphene BPA (III) salt rixx (finale product) |
|---|---|
| Z-isomer = 1.64 A/A % | Z-isomer = 0.07 A/A % |
| Z-isomer = 0.79 A/A % | Z-isomer = 0.03 A/A % |

Example 3: Preparation of Enclomiphene Citrate of Formula (I), Having a Needle Shaped Crystal Habit, Starting from Enclomiphene BPA Salt of Formula (III)

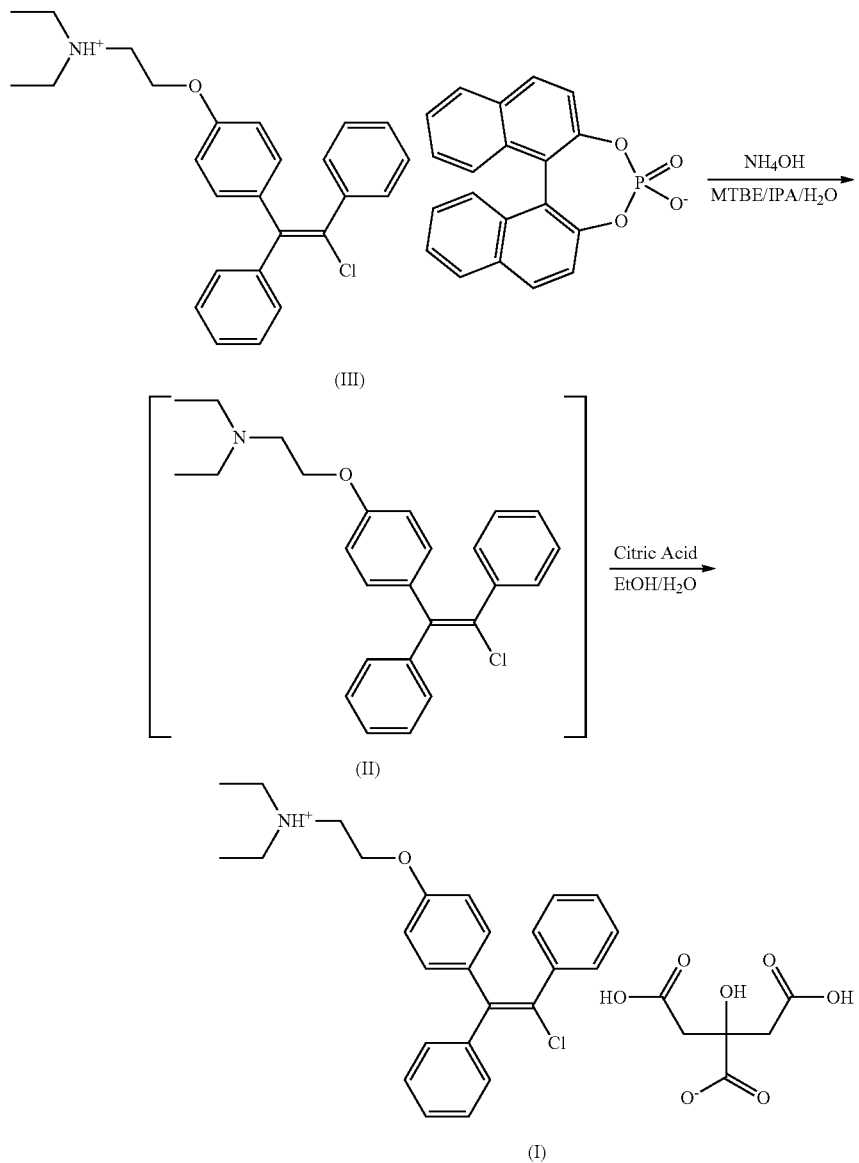

Into a proper 4 L reactor, equipped with propeller, temperature probes, condenser; Enclomiphene BPA salt of formula (III) (400 g, assay 99.8 wt % 0.528 mol, 1 equiv.) was suspended in methyl-tert-butyl ether (MTBE, 2 L), isopropanol (IPA, 0.5 L) and water (2 L). The mixture was stirred for 15 minutes, then 0.48 L of ammonia solution 30 wt % was added and the mixture was further stirred for one hour. The aqueous phase was separated and the organic layer was washed with a solution of ammonia solution 30 wt % (0.12 L) and water (0.6 L). The aqueous phase was separated and the organic layer was finally washed with water (0.6 L). The organic solution was evaporated to residue under vacuum at 60-65° C. The residue was dissolved in 1.36 L of absolute ethanol. The assay of the solution was determined at this stage through a potentiometric titration and results in 15.125 wt % as Enclomiphene of formula (II) (0.466 mol). Then 0.24 L of water were added and the solution was heated to 65° C. Meanwhile, citric acid monohydrate (100.8 g, 0.475 mol, 1.02 equiv.) was dissolved in absolute ethanol (1.7 L) and water (0.3 L), the solution was heated to 65° C. The solution of citric acid was dropped into the solution of Enclomiphene (II), while maintaining 65° C. The dosage takes place in 30-40 minutes. The inner temperature was decreased very slowly to 60° C. over 80 minutes, then it was further decrease to 55° C. over 40 minutes. When the inner temperature was in the range 60-55° C. (typically at 58° C.), the crystallization mixture was seeded with Enclomiphene citrate needle-shaped and a white product began to precipitate. Once reached 55° C. the temperature was further decreased to 30° C. over 30 minutes, then to 0° C. over 30 minutes. The slurry was stirred at 0° C. for at least two hours, then it was filtered and the wet cake was washed with 0.4 L of absolute ethanol. The product was dried under vacuum at 65° C. At the end of drying, 269 g of Enclomiphene citrate of formula (I) as needle crystal were isolated, corresponding to 91.8% molar yield.

HPLC Analysis (A/A %): 99.79% Enchlomiphene, 0.04% Z-Clomiphene (i.e. Z-isomer).

Example 4: Preparation of Enclomiphene Citrate of Formula (I), Having a Needle Shaped Crystal Habit, with a Mixture of Ethanol and Water, Wherein the Amount of Water is 15%

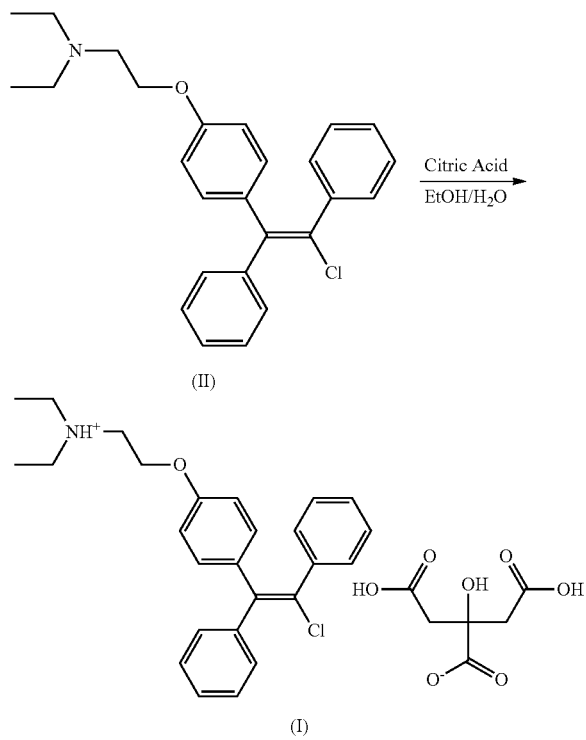

Into a proper 1 L reactor, equipped with propeller, temperature probes, condenser; Enclomiphene of formula (II) (15.0 g, assay 99.9 wt % 0.0369 mol, 1 equiv.) was dissolved in absolute ethanol (102 mL, 6.8 mL/g of free base), then 18 mL (1.2 mL/g of free base) of water were added and the solution was heated to 65° C. Meanwhile, citric acid monohydrate (7.92 g, 0.0377 mol, 1.02 equiv.) was dissolved in absolute ethanol (127 mL) and water (23 mL), the solution was heated to 65° C. The solution of citric acid was dropped into the solution of Enclomiphene (II), while maintaining 65° C. The dosage takes place in 30-40 minutes. The inner temperature was decreased very slowly to 60° C. over 80 minutes, then it was further decrease to 55° C. over 40 minutes. When the inner temperature was in the range 60-55° C. (typically at 58° C.), the crystallization mixture was seeded with Enclomiphene citrate needle-shaped and a white product began to precipitate. Once reached 55° C. the temperature was further decreased to 30° C. over 30 minutes, then to 0° C. over 30 minutes. The slurry was stirred at 0° C. for at least two hours, then it was filtered and the wet cake was washed with 30 mL of absolute ethanol. The product was dried under vacuum at 65° C. At the end of drying, 20.2 g of Enclomiphene citrate of formula (I) as needle crystal were isolated, corresponding to 91.4% molar yield.

HPLC Analysis (A/A %): 99.86% Enchlomiphene, 0.03% Z-Clomiphene.

Example 4a: Preparation of Enclomiphene Citrate of Formula (I), Having a Needle Shaped Crystal Habit, with a Mixture of Isopropanol and Water, Wherein the Amount of Water is 15%

Into a proper 1 L reactor, equipped with propeller, temperature probes, condenser; Enclomiphene of formula (II) (40.0 g, assay 99.9 wt % 0.0985 mol, 1 equiv.) was dissolved in isopropanol (272 mL, 6.8 mL/g of free base), then 48 mL (1.2 mL/g of free base) of water were added and the solution was heated to 65° C. Meanwhile, citric acid monohydrate (21.10 g, 0.100 mol, 1.02 equiv.) was dissolved in isopropanol (340 mL, 8.5 mL/g of free base) and water (60 mL, 1.5 mL/g of free base), the solution was heated to 65° C. The solution of citric acid was dropped into the solution of Enclomiphene (II), while maintaining 65° C. The dosage takes place in 30-40 minutes. The inner temperature was decreased very slowly to 60° C. over 80 minutes, then it was further decrease to 55° C. over 40 minutes. When the inner temperature was in the range 60-55° C. (typically at 58° C.), the crystallization mixture was seeded with Enclomiphene citrate needle-shaped and a white product began to precipitate. Once reached 55° C. the temperature was further decreased to 30° C. over 30 minutes, then to 0° C. over 30 minutes. The slurry was stirred at 0° C. for at least two hours, then it was filtered and the wet cake was washed with 30 mL of isopropanol. The product was dried under vacuum at 65° C. At the end of drying, 56.5 g of Enclomiphene citrate of formula (I) as needle crystal were isolated, corresponding to 95.9% molar yield.

Example 4b: Preparation of Enclomiphene Citrate of Formula (I), Having a Needle Shaped Crystal Habit, with a Mixture of n-Propanol and Water, Wherein the Amount of Water is 15%

Into a proper 0.5 L reactor, equipped with propeller, temperature probes, condenser; Enclomiphene of formula (II) (9.0 g, assay 99.9 wt % 0.0985 mol, 1 equiv.) was dissolved in n-propanol (61 mL, 6.8 mL/g of free base), then 11 mL (1.2 mL/g of free base) of water were added and the solution was heated to 65° C. Meanwhile, citric acid monohydrate (4.70 g, 0.0224 mol, 1.02 equiv.) was dissolved in n-propanol (77 mL, 8.5 mL/g of free base) and water (14 mL, 1.5 mL/g of free base), the solution was heated to 65° C. The solution of citric acid was dropped into the solution of Enclomiphene (II), while maintaining 65° C. The dosage takes place in 30-40 minutes. The inner temperature was decreased very slowly to 60° C. over 80 minutes, then it was further decrease to 55° C. over 40 minutes. When the inner temperature was in the range 60-55° C. (typically at 58° C.), the crystallization mixture was seeded with Enclomiphene citrate needle-shaped and a white product began to precipitate. Once reached 55° C. the temperature was further decreased to 30° C. over 30 minutes, then to 0° C. over 30 minutes. The slurry was stirred at 0° C. for at least two hours, then it was filtered and the wet cake was washed with 30 mL of n-propanol I. The product was dried under vacuum at 65° C. At the end of drying, 11.7 g of Enclomiphene citrate of formula (I) as needle crystal were isolated, corresponding to 88.1% molar yield

Example 4c: Preparation of Enclomiphene Citrate of Formula (I), Having a Needle Shaped Crystal Habit, with a Mixture of n-Butanol and Water, Wherein the Amount of Water is 15%

Into a proper 0.5 L reactor, equipped with propeller, temperature probes, condenser; Enclomiphene of formula (II) (9.0 g, assay 99.9 wt % 0.0985 mol, 1 equiv.) was dissolved in n-butanol (61 mL, 6.8 mL/g of free base), then 11 mL (1.2 mL/g of free base) of water were added and the solution was heated to 65° C. Meanwhile, citric acid monohydrate (4.70 g, 0.0224 mol, 1.02 equiv.) was dissolved in n-butanol (77 mL, 8.5 mL/g of free base) and water (14 mL, 1.5 mL/g of free base), the solution was heated to 65° C. The solution of citric acid was dropped into the solution of Enclomiphene (II), while maintaining 65° C. The dosage takes place in 30-40 minutes. The inner temperature was decreased very slowly to 60° C. over 80 minutes, then it was further decrease to 55° C. over 40 minutes. When the inner temperature was in the range 60-55° C. (typically at 58° C.), the crystallization mixture was seeded with Enclomiphene citrate needle-shaped and a white product began to precipitate. Once reached 55° C. the temperature was further decreased to 30° C. over 30 minutes, then to 0° C. over 30 minutes. The slurry was stirred at 0° C. for at least two hours, then it was filtered and the wet cake was washed with 30 mL of n-butanol. The product was dried under vacuum at 65° C. At the end of drying, 11.6 g of Enclomiphene citrate of formula (I) as needle crystal were isolated, corresponding to 87.4% molar yield.

Example 4d: Preparation of Enclomiphene Citrate of Formula (I), Having a Needle Shaped Crystal Habit, with a Mixture of Tert-Butanol and Water, Wherein the Amount of Water is 15%

Into a proper 0.5 L reactor, equipped with propeller, temperature probes, condenser; Enclomiphene of formula (II) (9.0 g, assay 99.9 wt % 0.0985 mol, 1 equiv.) was dissolved in tert-butanol (61 mL, 6.8 mL/g of free base), then 11 mL (1.2 mL/g of free base) of water were added and the solution was heated to 65° C. Meanwhile, citric acid monohydrate (4.70 g, 0.0224 mol, 1.02 equiv.) was dissolved in tert-butanol (77 mL, 8.5 mL/g of free base) and water (14 mL, 1.5 mL/g of free base), the solution was heated to 65° C. The solution of citric acid was dropped into the solution of Enclomiphene (II), while maintaining 65° C. The dosage takes place in 30-40 minutes. The inner temperature was decreased very slowly to 60° C. over 80 minutes, then it was further decrease to 55° C. over 40 minutes. When the inner temperature was in the range 60-55° C. (typically at 58° C.), the crystallization mixture was seeded with Enclomiphene citrate needle-shaped and a white product began to precipitate. Once reached 55° C. the temperature was further decreased to 30° C. over 30 minutes, then to 0° C. over 30 minutes. The slurry was stirred at 0° C. for at least two hours, then it was filtered and the wet cake was washed with 30 mL of tert-butanol. The product was dried under vacuum at 65° C. At the end of drying, 11.2 g of Enclomiphene citrate of formula (I) as needle crystal were isolated, corresponding to 84.4% molar yield.

Example 5: Preparation of Enclomiphene Citrate of Formula (I), Having a Needle Shaped Crystal Habit. Preparation of the Seed Crystal Into a proper 1 L reactor, equipped with propeller, temperature probes, condenser; Enclomiphene of formula (II) (15.0 g, assay 99.9 wt % 0.0369 mol, 1 equiv.) was dissolved in absolute ethanol (102 mL, 6.8 mL/g of free base), then 18 mL (1.2 mL/g of free base) of water were added and the solution was heated to 65° C. Meanwhile, citric acid monohydrate (7.92 g, 0.0377 mol, 1.02 equiv.) was dissolved in absolute ethanol (127 mL, 8.5 mL/g of free base) and water (23 mL 1.5 mL/g of free base), the solution was heated to 50° C. The solution of citric acid was dropped into the solution of Enclomiphene (II), while maintaining 50° C. The dosage takes place in 30-40 minutes. At the end of the dosage, the stirring was turned off and the mixture was allowed to cool down to room temperature without stirring. The product began to crystallize at 40-30° C. Once reached 20-25° C. the stirring was turned on and the temperature was further decreased to 0° C. over 30 minutes. The slurry was stirred at 0° C. for at least two hours, then it was filtered and the wet cake was washed with 30 mL of absolute ethanol. The product was dried under vacuum at 65° C. At the end of drying, 13.9 g of Enclomiphene citrate of formula (I) were isolated, corresponding to 62.3% molar yield

Example 6: Preparation of Enclomiphene Citrate of Formula (I), Having a Non-Needle Shaped Crystals, with a Mixture of Acetone and Water, Wherein the Amount of Water is 15%

Comparative example (see FIG. 8) and evidence example of the invention. Following the same process described in the example 4, substituting ethanol solvent with acetone solvent. Starting from 15.0 g of Enclomiphene of formula (II), following the above mentioned process, 22.3 g of Enclomiphene citrate of formula (I) were isolated, corresponding to 94.2% molar yield product. For the morphology of the crystal see FIG. 8.

Indeed, the microscopy analysis provides a better further evidence of the crystal habit of Enclomiphene citrate (I) of the example 6 (see FIG. 8) which has a form more different than/to Enclomiphene citrate (I) having a needle shaped crystal habit, obtained according to above described examples, i.e. 4, 4a, 4b, 4c, 4d (see FIGS. 5, 6 and 7).

HPLC Analysis (A/A %): 99.63% Enchlomiphene, 0.20% Z-Clomiphene.

Example 7: Analytical Method to Identify and Quantify Z-Clomiphene of Formula (IV) into Enclomiphene of Formula (II) or Enclomiphene Citrate of Formula (I) or Enclomiphene BPA Salt of Formula (III) and for Determining the Chemical Purity Chromatographic Conditions:

Dim. Column: 250 mm×4.6 mm, 5 μm

Stationaly phase: Butyl sylane (USP phase L26, Vydac 4C is suggested)

Temp. Column: room temperature

Mobile Phase: Methanol/water/triethylamine 55: 45: 0.3 v/v

Adjust at pH 2.5 with phosphoric acid

Flow: 1.0 mL/min

Detector UV a 233 nm,

Injection Volume: 10 μL

Sample diluent: mobile phase.

Applying the conditions described above the expected retention times are as indicated below:

| Compound | RRT |
| --- | --- |
| Z-Clomiphene | 1.00 |
| Enclomiphene | 1.09 |

Example 8: Characterization of the Solid Form of Enclomiphene Citrate Having Non-Needle Crystal Habit, being Soft Polycrystalline Agglomerates, Prepared According to Example 6

Crystal Habit

The solid form of Enclomiphene citrate has non-needle shaped crystal habit. Moreover, Enclomiphene citrate shows a crystalline habit as soft polycrystalline agglomerates.

DSC

DSC analysis was recorded with a Mettler DSC822e. A sample of 3.2140 mg was weighed into a 40 μL aluminium crucible with a pinhole lid and was heated, under nitrogen (50 mL/min), at 10° C./min from 30 to 300° C.

The solid form of Enclomiphene citrate is characterized by an endothermic peak corresponding to the melting point with an onset at 146.31° C. (fusion enthalpy −98.96 J/g), measured by DSC analysis (10° C./min). At 148.91° C. (onset) begin a broad endotermic peak.

Example 8-bis: Microscopy Analysis of Crystal Habits of Enclomiphene Citrate of Formula (I)

The products were observed in a stereoscopic microscope Leica MZ16F and the pictures were obtained using a Leica DCF 300 FX camera. Reflected and transmitted light was used, if not specified images were taken with reflected light. For each image, the scale is specified in the picture itself.

1. Microscopy analysis of Enclomiphene citrate having non-needle crystal habit, having m.p. 146° C. (by DSC) (as prepared in example 6).

Enclomiphene citrate crystallized with a mixture of a acetone and 15% v/v water, with m.p. 146° C. (by DSC) (as prepared in example 6) presents a crystal habit forming soft polycrystalline agglomerates (see FIG. 8). Fragments are plates or flakes. The solid is not transparent and does not present smooth sides. It is not possible to observe individual shape of crystals due to its small size.

2. Microscopy analysis of Enclomiphene citrate having needle shaped crystal habit, having m.p. 149° C. (by DSC) (as prepared in example 4).

Enclomiphene citrate (I) having needle-shaped crystal habit, crystallized with a mixture of ethanol and 15% v/v of water, with m.p. 149° C. (by DSC) (as prepared in example 4) presents a crystal habit of long needle crystal (see FIGS. 5, 6 and 7). Individual crystals, like needles, only, in particular, long needles. Needles are in a great amount and have big size/or length, indeed, as shown FIG. 8, they are overlapping, but they are monocrystalline.

3. Morphology and size comparison of Enclomiphene citrate (I) having needle-shaped and having non-needle crystal habit.

The two products of Enclomiphene citrate present a polycrystalline structure when they were observed at microscope, in one case the long crystals were needles (crystals from a mixture of ethanol and from 10% v/v to 40% v/v of water) and in the other case (crystals from a mixture of acetone and 15% v/v of water) the crystal shape was not determined but the crystal shape of the two forms is different.

In conclusions, microscopy analysis showed that crystals obtained with a mixture of ethanol and from 10% v/v to 40% v/v of water presents a structure formed by big/long needles.

Example 9: Characterization of Enclomiphene Citrate Having Needle Shaped Crystal Habit XRPD analysis was performed using a PANalytical X'Pert diffractometer with Cu Kα radiation in Bragg-Brentano geometry. The system is equipped with a monodimensional, real time multiple strip detector. The diffractogram was recorded from 3° to 40° (2θ) at a scan rate of 0.0205° per second.

Figure 1:
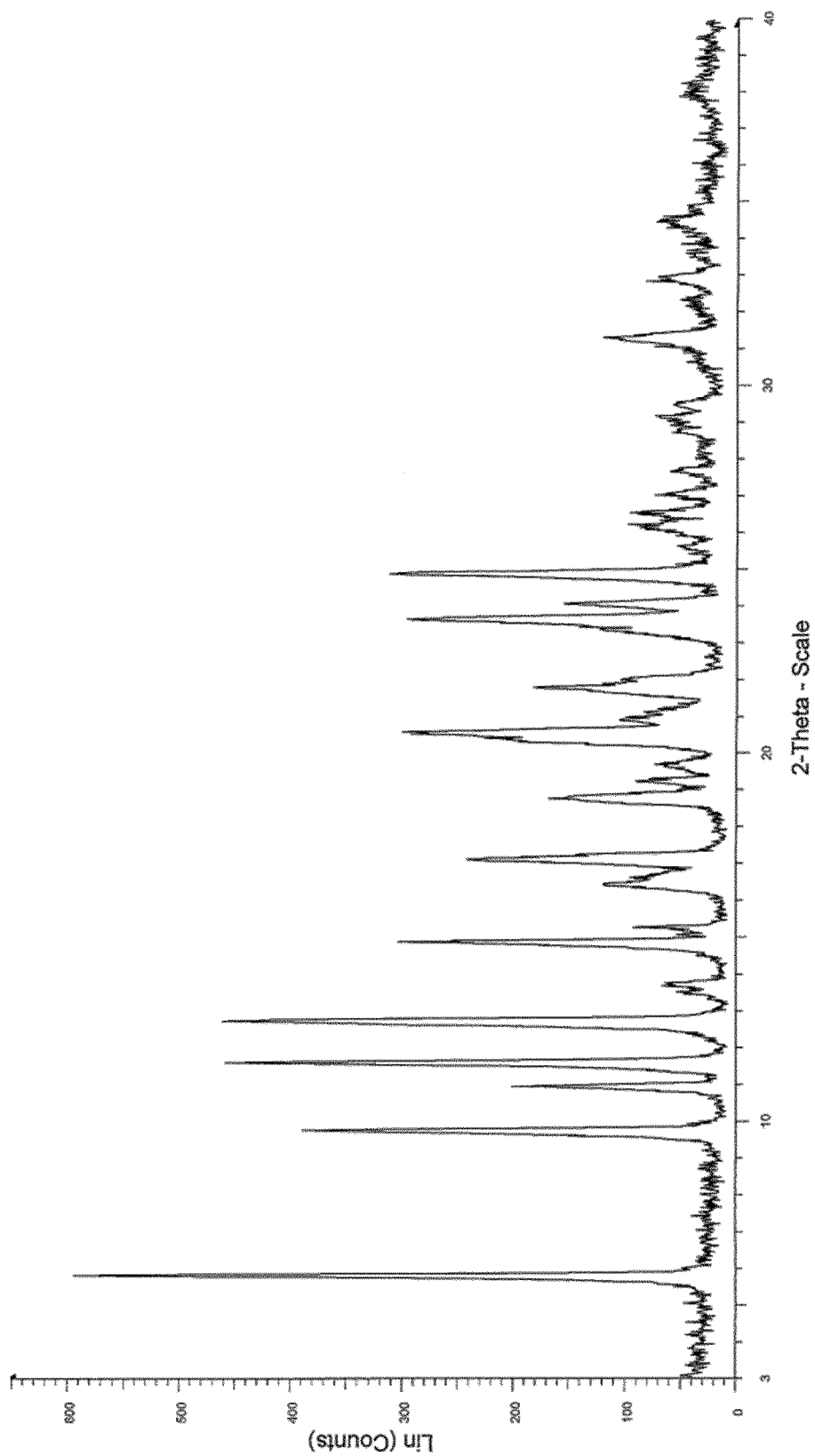
FIG. 1 shows the XPRD diffractogram of the solid form of Enclomiphene citrate having needle crystal habit obtained by crystallization from a mixture of ethanol and 15% v/v water.

2. Enclomiphene citrate having needle crystal habit (as prepared i.e. in example 4) was analyzed and the XRPD diffractogram, acquired before and after a gentle milling treatment (in order to confirm that crystalline morphology was not affected by a gentle milling treatment, which is the case), is shown in FIG. 1.

In particular, Enclomiphene citrate having needle crystals habit has a characteristic X-ray powder diffraction pattern with characteristic peaks expressed in 2-Theta values (2θ) at: 5.8, 11.5, each peak ±0.1.

More in particular, Enclomiphene citrate having needle crystals habit has a characteristic X-ray powder diffraction pattern with characteristic peaks expressed in 2-Theta values (2θ) at: 5.8, 11.5, 12.7, 14.9 and 24.9, each peak ±0.1.

Again more particularly, Enclomiphene citrate having needle crystals habit has a characteristic X-ray powder diffraction pattern with characteristic peaks expressed in 2-Theta values (2θ) at: 5.8, 9.7, 10.9, 11.5, 12.7, 14.9, 17.1, 20.6, 21.8, 23.6, 23.7 and 24.9, each peak ±0.1.

In particular, using the peak at 2-Theta value (2θ) 12.7° as peak intensity reference, it is clear that peaks at 5.8° and 11.5° (2θ) of the sample of Enclomifene citrate having needle shaped crystal habit have much more higher relative intensities than sample of Enclomifene citrate having non-needle shaped crystal habit, while the other peaks have similar intensity.

In the case of Enclomifene citrate having needle shaped crystal habit, this difference of intensity comes from the orientation preferential of the crystals caused by the needle shape.

Example 10: Studies of Solubility of Enclomiphene Citrate Crystal Habits Forms To determine the effect of the crystal size and morphology over the solubility of the different solid forms of Enclomiphene citrate, kinetic solubility studies were carried out in water and buffered aqueous solutions. Solubility was determined by HPLC analysis, by comparison of the area corresponding to Enclomiphene HPLC peak.

For each solubility study, the following parameters were monitored:

intensity of Enclomiphene peak for each replicate of the assay
average value
standard deviation.

Experimental Procedure

To carry out the solubility studies, 400 mg of each product (not grinded) was stirred in water (24 ml, 60v) under the same conditions of stirring speed (magnetic stirring at 1000 rpm with a 2 cm "rugby shape" stir bar), flask used (round bottom flask of 50 ml of capacity with a 29/32 neck), etc. Alliquotes of ca 6 ml of suspension were filtered at different times: 15, 45, 90 and 180 min. After filtration, mother liquors were directly analyzed by HPLC (doing 2 replicates for each analysis) and its pH was determined. The filtered solid was analyzed by XRPD. The solubility analysis was repeated for each product and comparison of solubility was determined by the differences of HPLC area.

Below an HPLC method that allow to have a fast determination of Enclomiphene solubility:

| | |
|---|---|
| Column | C18 Zorbax Eclipse (XDB) 150 × 4.6 mm, 5 micron |
| Mobile phase | ($H_2O$-$H_3PO_4$ 0.1%:ACN 95:5)/ACN (60:40)-6 min-(30:70)-3 min-(30:70); Post run 3 min |
| Temperature | 25° C. |
| Flow | 1.5 mL/min |
| Wavelength | 240 nm |
| Injection volumen | 25 microliters of mother liquors |
| Stop time | 9 min (+3 min de post time) |
| Retention time | Rt (Enclomiphene) = 3.1 min |
| | Rt (citric acid) = 0.9 min |

These HPLC conditions were used to perform solubility analysis.

Solubility Studies in Water

Initially the solubility of Enclomiphene citrate in water was carried out by duplicate. However as we observed a high standard variation for some HPLC analysis between both duplicates, these assays were done by triplicate. For each Enclomiphene citrate samples, the results are shown in the following tables: Table 1 for Enclomiphene citrate having non-needle crystals (m.p. 146° C.), lot 722, and Table 2 for Enclomiphene citrate having needle crystals (m.p. 149° C.), lot 723.

Table 1. Results of water solubility studies of Enclomiphene citrate having non-needle crystals:

| Time min | HPLC a/a | HPLC a/a | HPLC a/a | average HPLC a/a | SD |
|---|---|---|---|---|---|
| 0 | 0 | 0 | 0 | 0 | 0 |
| 15 | 1819 | 3483 | 3273 | 2858 | 906 |
| 45 | 3083 | 3370 | 3225 | 3226 | 144 |
| 90 | 3229 | 2099 | 2988 | 2772 | 595 |
| 180 | 2991 | 3597 | 3208 | 3265 | 307 |

Table 2. Results of water solubility studies of Enclomiphene citrate having needle crystals:

| Time min | HPLC a/a | HPLC a/a | HPLC a/a | average a/a | SD |
|---|---|---|---|---|---|
| 0 | 0 | 0 | 0 | 0 | 0 |
| 15 | 4099 | 6104 | 3273 | 5152 | 1006 |
| 45 | 5206 | 5457 | 3225 | 4962 | 652 |
| 90 | 5085 | 5426 | 2988 | 5334 | 218 |
| 180 | 4120 | 5327 | 3208 | 4126 | 1198 |

Figure 10:
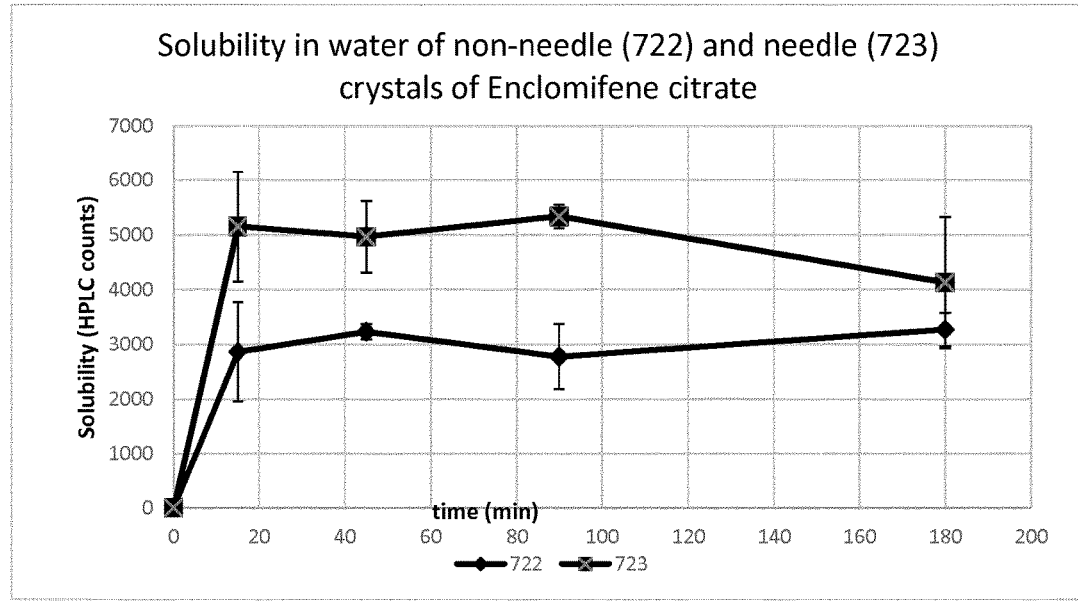
FIG. 10 shows the HPLC A/A average values of solubility of the two solid forms of Enclomiphene citrate needle vs non-needle plotted against time.

The HPLC a/a average values of solubility of the two solid forms of Enclomiphene citrate were plotted against time (shown FIG. 10)

Solubility of Enclomiphene citrate having needle shaped crystal habit is higher than Enclomiphene citrate having non-needle shaped crystal habit over three hours, although this difference of solubility seems to decrease with time. Indeed the solubility of needle crystals seems to decrease with time and could be similar to the solubility of non-needle crystals after 3 hour taking into consideration the experimental error from the different replicates (SD). Therefore the crystal size and habit of Enclomiphene citrate with needle crystals seems to produce a higher kinetic solubility that decreases with time affording after three hour a solubility similar to of Enclomiphene citrate having non-needle crystals. However Enclomiphene citrate having needle shaped crystal habit is more soluble (almost two times) than Enclomiphene citrate having non-needle shaped crystal habit.

Solubility Studies at pH 4.5

Solubility at a slightly acid medium was determined at pH 4.5 buffer used was a mixture acetic acid/sodium acetate prepared according to USP specifications.

The solubility of Enclomiphene citrate having non-needle and needle crystals in 4.5 pH buffer was carried out by duplicate. In this case the reproducibility was better than in the analysis of citrates with water.

The results are shown in the following tables (Table 3 for Enclomiphene citrate having non-needle, lot 722, and Table 4 for Enclomiphene citrate having needle crystals, lot 723).

Table 3. Results of solubility study of Enclomiphene citrate having non-needle crystals at pH=4.5.

| Time min | HPLC a/a | HPLC a/a | Average a/a | SD |
|---|---|---|---|---|
| 0 | 0 | 0 | 0 | 0 |
| 15 | 1294 | 1077 | 1185 | 154 |
| 45 | 907 | 941 | 924 | 24 |
| 90 | 1279 | 912 | 1095 | 260 |
| 180 | 1008 | 1096 | 1052 | 62 |

Table 4. Results of solubility study of Enclomiphene citrate having needle crystals at pH=4.5.

| Time min | HPLC a/a | HPLC a/a | Average a/a | SD |
|---|---|---|---|---|
| 0 | 0 | 0 | 0 | 0 |
| 15 | 3941 | 4330 | 4135 | 275 |
| 45 | 3978 | 4070 | 4024 | 65 |
| 90 | 4889 | 5329 | 5109 | 311 |
| 180 | 5098 | 5060 | 5079 | 27 |

Figure 11:
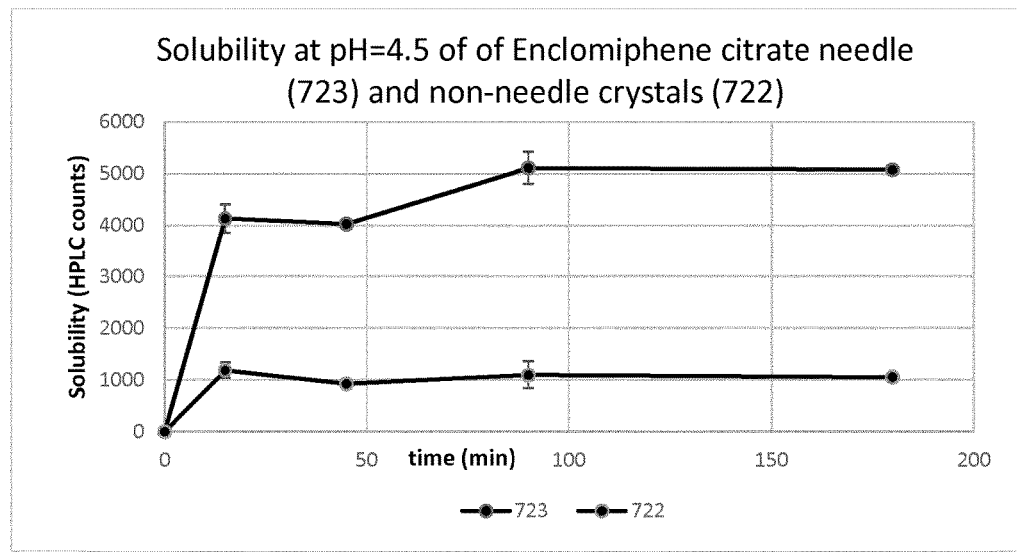
FIG. 11 shows HPLC A/A average values of solubility of the two solid forms of Enclomiphene citrate needle vs non-needle were plotted against time (shown FIG. 11)
Figure 12:
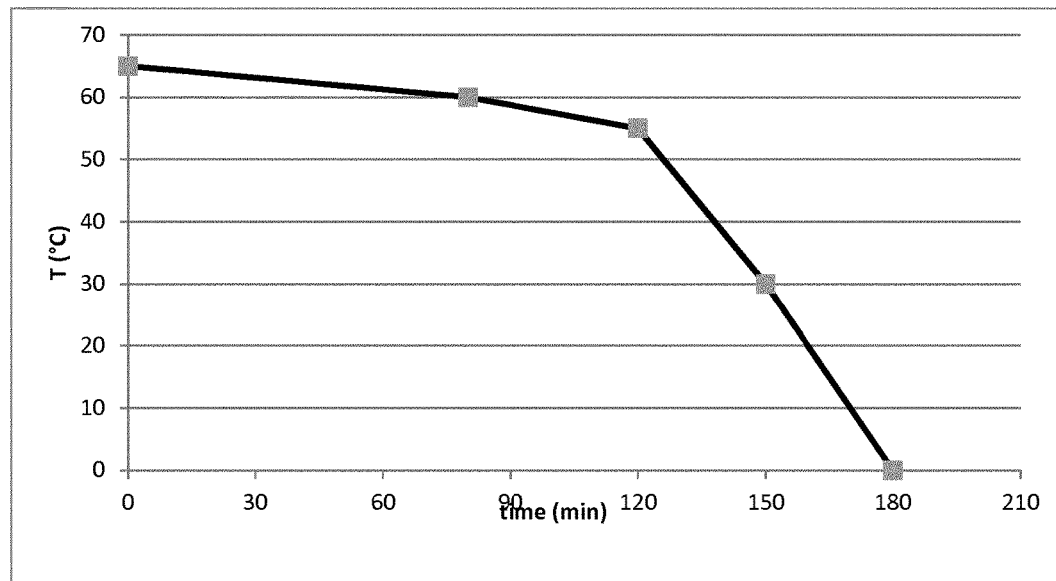
FIG. 12 shows the optimum temperature cooling ramp for obtaining Enclomiphene citrate having needle crystal habit, according to the process of the present invention.

The HPLC A/A average values of solubility of the two solid forms of Enclomiphene citrate were plotted against time (shown FIG. 11).

From the plot above, it can be observed very different dissolution curves between the two Enclomiphene citrate crystal habit forms. The solubility of Enclomiphene citrate having needle crystals (lot 723) was about 4 to 5 times higher than solubility of Enclomiphene citrate having non-needle crystals (lot 722) and this difference of solubility seems to increase or maintain with time. Therefore in this case, the differences in the crystal size and habit play a crucial role in determining the solubility of Enclomiphene citrate.

Thus, Enclomiphene citrate having needle crystals of the present invention is much more soluble at pH 4.5 than Enclomiphene citrate having non-needle crystals, in particular about 4 to 5 times more soluble.

Therefore, either in water and at pH 4.5 Enclomiphene citrate having needle crystals of the present invention is more soluble than Enclomiphene citrate having non-needle crystals. However, the extent of this effect is much more evident in a pH 4.5 buffered solution than in pure water.

Example 11: Study Hygroscopicity of Enclomiphene Citrate Crystal Habits

The hygroscopicity of the different batches of Enclomiphene citrate was determined by DVS (Dynamic Vapour Sorption) with a Q5000 TA instrument. This is a gravimetric technique that measures how much water is absorbed or desorbed by a sample at different relative humidity (RH). At each RH, the sample mass must be allowed to reach gravimetric equilibrium (or surpassed time limit) before progressing to the next humidity level. Sorption and desorption isotherms will be performed at 25° C. over a range of 0-95% RH. The type of sorption isotherm is determined by the pore size and surface character of the material.

DVS was performed with 12.2509 mg of Enclomiphene citrate batch 722 and 13.5772 mg of Enclomiphene citrate batch 723 with the following conditions:

Gravimetric equilibration at 25° C.-0% RH
Increase to the next RH % level when gravimetric variation is inferior to 0.01% after 20 min or when the equilibration time surpasses the time limit of 300 min.

Batch 722—Enclomiphene citrate having non-needle crystal habit.

DVS analysis of batch 722 indicates significant moisture sorption between 0% and 65% RH (+2% weight). The water uptake then increases more drastically to reach 6% weight at 95% RH. The adsorption and desorption profiles are essentially overlapped indicating that the moisture "picked-up" at higher humidities should be adsorbed onto the surface of the material and does not affect its internal structure.

The sorption has a sigmoidal shape characteristic of Type II isotherms. The amount of vapor adsorbed increases rapidly at lower relative pressures, showing a profile concave with respect to the x-axis. At higher relative pressures, the curve assumes a shape convex with respect to the x-axis. The turning point of the curve is usually considered as the completion of the monomolecular layer and the beginning of the formation of multi-molecular layers of adsorbate on the surface.

Batch 723—Enclomiphene citrate having needle crystal habit.

DVS analysis of batch 723 indicates significant moisture sorption between 0% and 95% RH (+2.33% weight). The sorption and desorption profiles are overlapped indicating that the moisture "picked-up" at higher humidities should be adsorbed onto the surface of the material and does not affect its internal structure.

As for Enclomiphene citrate batch 722, the sorption has a sigmoidal shape characteristic of Type II isotherms.

Comparison batches 722 and 723.

The hygroscopicity of Enclomiphene citrate batches 722 and 723 is identical between 0 and 65% RH. Then the hygroscopicity increases strongly in the case of batch 722, i.e. for Enclomiphene citrate having non-needle crystal habit, up to 6% at 95% RH, while it increases moderately in the case of batch 723, i.e. for Enclomiphene citrate having needle crystal habit achieving 2.3% at 95% RH (See FIG. 9).

Thus, Enclomiphene citrate having needle shaped crystal habit, shows much better hygroscopicity behavior in comparison to Enclomiphene citrate having non-needle shaped crystal habit, especially at relative humidity higher than 65%.

Example 12: Characterization of Enclomiphene Citrate of Formula (I) Having Needle Shaped Crystal Habit by Chord-Length Distribution Analysis The Chord-length distribution analysis is a type of particle size analysis which use Focused Beam Reflectance Measurement (FBRM). In particular, measures a fingerprint distribution of the particle system that is sensitive to changes in dimension, shape and count by a specific probes. Real-time measurements track changes in particles as they naturally exist in the process eliminating the need for offline sampling.

Specifically, the chord-length distribution of Enclomiphene citrate of formula (I) was determined by ParticleTrack G400 with FBRM® with PVM probe, technology for real-time quantitative measurement provided by Mettler-Toledo.

Repeating the process described in the example 4 with the addition of PVM probe at the beginning, therefore equipping the reactor equipped with propeller, temperature probes, condenser and said PVM probe the following results have been collected.

Figure 13:
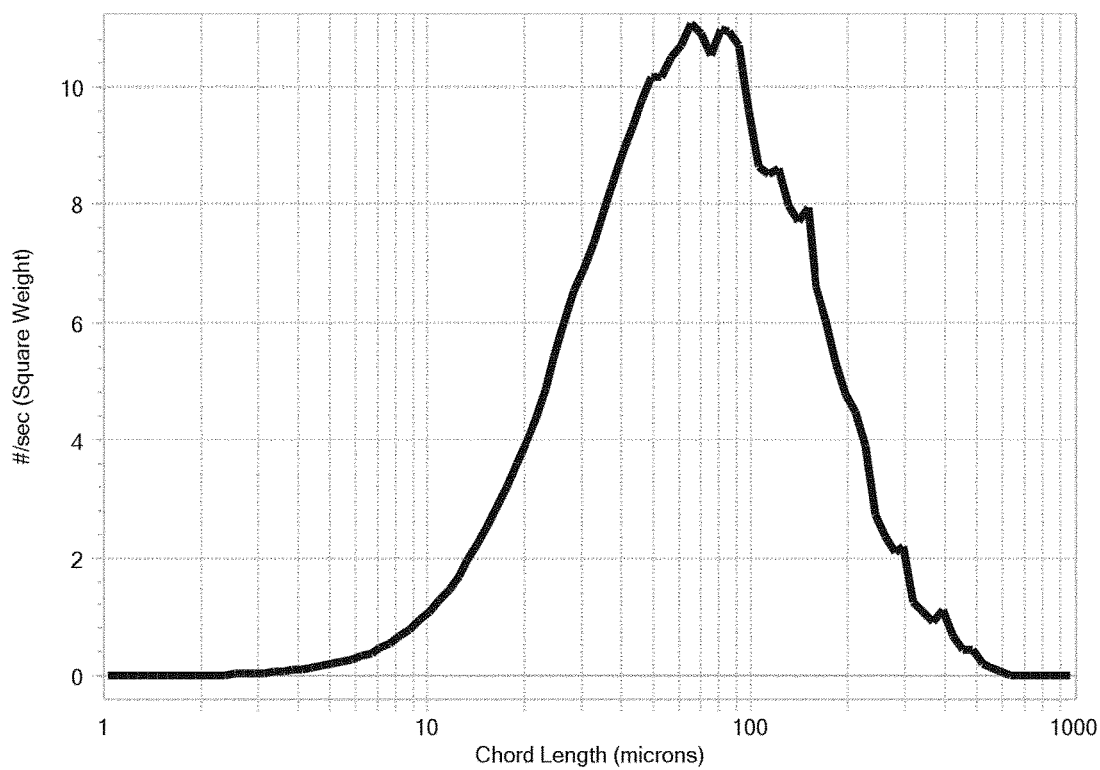
FIG. 13 shows iC FBRM analysis with PVM probe of Enclomiphene citrate having needle shape crystal habit, obtained from the process of the invention.

The final distribution obtained by FBRM® with PVM probe is shown in the FIG. 13 and relative data are reported in the following table:

| Statistics | |
|---|---:|
| Mean Square Weight | 87.30 |
| counts/sec No Wt 1-1000 | 29,108.35 |
| counts/sec No Wt 1-50 | 27,104.27 |
| counts/sec n No Wt 50-150 | 1,912.88 |
| counts/sec No Wt 150-1000 | 91.20 |

The mean square weight described in the present application are thus measured according to the procedure described in the present example.

Example 13: Micronization of Enclomiphene Citrate of Formula (I) Having Needle Shaped Crystal Habit Enclomiphene citrate of formula (I) having needle shaped crystal habit (300 g) was dropped into an Micronized air-jett mill (model: MICRONETTE da LABORATORIO "M.100", provided by Nuova Guseo (Villanova sull'Arda (PC), Italy)) and was then micronized.

The micronized Enclomiphene citrate was analyzed by Particle size distribution (PSD).

In particular, particle size distribution was determined with a Beckman Coulter LS13320 apparatus equipped with an Universal Liquid Module.

Particle size distribution of micronized Enclomiphene citrate shows a gaussian distribution with the mean value at 12 µm. D50 value was 10 µm.

The invention claimed is:

1. A process for the preparation of Enclomiphene citrate of formula (I):

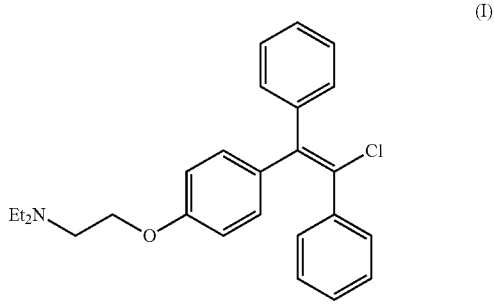

-continued

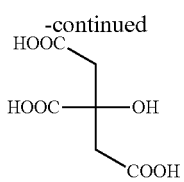

having needle shaped crystal habit,
comprising crystallizing of Enclomiphene citrate of formula (I) with a mixture of a C2-C5 alkyl alcohol and water, wherein the amount of water is between 10% and 40% v/v.

2. Process according to the claim 1, wherein the C2-C5 alkyl alcohol is ethanol or isopropanol.

3. Process according to claim 1, wherein the amount of water is comprised between 12% and 20% v/v.

4. Process according to claim 1, wherein the amount of water is 15% v/v.

5. Process according to claim 1, wherein the amount of mixture of a C2-C5 alkyl alcohol and water is between 10 and 15 volumes referred to the amount of Enclomiphene citrate (I).

6. Process according to claim 1, wherein the temperature at the beginning of the crystallizing is between 60° C. and 70° C.

7. Process according to claim 1, wherein during the crystallizing, the temperature decreases from a temperature in the range of 60° C. to 70° C. to 0° C. in 3 hours.

8. Process according to claim 1, wherein the crystallizing is seeded at a temperature between 60° C. and 55° C. with Enclomiphene citrate of formula (I) having needle shaped crystal.

9. Process according to claim 1, wherein Enclomiphene citrate of formula (I) is prepared by addition of citric acid to a solution of Enclomiphene of formula (II):

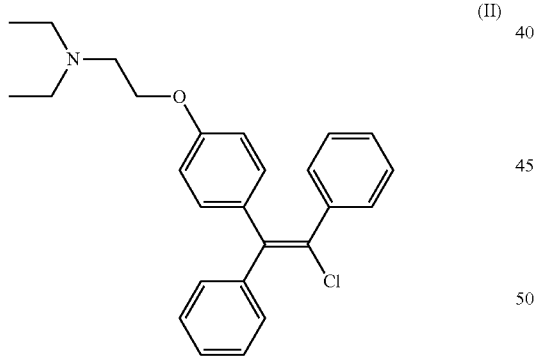

(II)

wherein the solution is the mixture of an C2-C5 alkyl alcohol and water.

10. Process according to the claim 9, wherein the citric acid is solubilized into a mixture of the C2-C5 alkyl alcohol and water.

11. Process according to claim 9, wherein the solution of Enclomiphene of formula (II) and the solution wherein the citric acid is solubilized are the same mixture of a C2-C5 alkyl alcohol and water.

12. Process according to claim 9, wherein the amount of mixture of a C2-C5 alkyl alcohol and water of the solution of Enclomiphene of formula (II) is between 5 and 6 volumes referred to the amount of Enclomiphene citrate (I).

13. Process according to claim 9, wherein the addition of citric acid is carried out at a temperature between 60° C. and 70° C.

14. Process according to claim 1, comprising the further steps:
a) converting Enclomiphene BPA salt of formula (III):

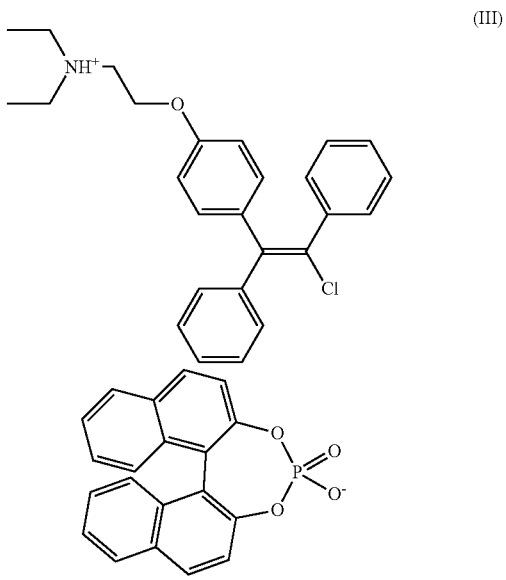

(III)

to Enclomiphene of formula (II):

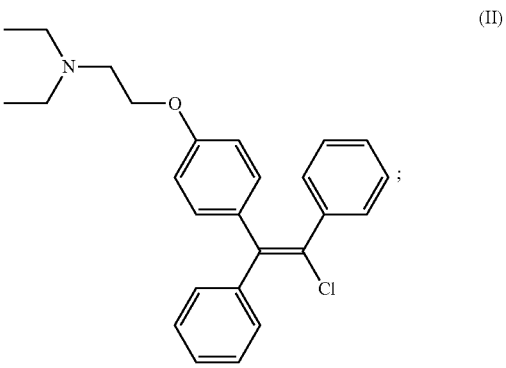 [SMILES: CCN(CC)CCOc1ccc(/C(=C(/Cl)c2ccccc2)c2ccccc2)cc1]

(II)

and
b) converting the Enclomiphene of formula (II) obtained in step a) to Enclomiphene citrate of formula (I).

15. Process according to the claim 14, wherein the Enclomiphene of formula (II) obtained in step a) is not isolated as solid.

16. Process according to claim 14, further comprising the step of purifying of the Enclomiphene BPA salt of formula (III) by recrystallizing the Enclomiphene BPA salt of formula (III) or by converting of said salt to Enclomiphene of formula (II) and then re-preparing the Enclomiphene BPA salt of formula (III).

17. Process according to claim 1, wherein the Enclomiphene citrate of formula (I) has needle shaped crystal habit and has mean square weight in the range of from 60 μm to 120 μm and/or is in the form of only needle crystals.

* * * * *